(12) United States Patent
Isaac et al.

(10) Patent No.: US 7,772,235 B2
(45) Date of Patent: Aug. 10, 2010

(54) MGLUR5 MODULATORS

(75) Inventors: Methvin Isaac, Brampton (CA);
Abdelmalik Slassi, Mississauga (CA);
Louise Edwards, Mississauga (CA);
Peter Dove, Toronto (CA); Tao Xin, Toronto (CA); Tomislav Stefanac, Burlington (CA)

(73) Assignee: Astrazeneca AB, Sodertalje (SE)

( * ) Notice: Subject to any disclaimer, the term of this patent is extended or adjusted under 35 U.S.C. 154(b) by 336 days.

(21) Appl. No.: 11/902,784

(22) Filed: Sep. 25, 2007

(65) Prior Publication Data
US 2008/0125436 A1 May 29, 2008

Related U.S. Application Data

(60) Provisional application No. 60/828,325, filed on Oct. 5, 2006.

(51) Int. Cl.
*A61K 31/50* (2006.01)
*A61K 31/44* (2006.01)
*C07D 403/14* (2006.01)
*C07D 413/14* (2006.01)

(52) U.S. Cl. .................. 514/252.05; 544/224; 544/238; 544/239; 546/268.1; 546/268.4; 546/269.1; 514/247; 514/252.01; 514/336; 514/340

(58) Field of Classification Search ................. 544/224, 544/238, 239; 546/268.1, 268.4, 269.1; 514/247, 252.01, 252.05, 336, 340
See application file for complete search history.

(56) References Cited

U.S. PATENT DOCUMENTS 7,456,200 B2 * 11/2008 Arora et al. .................. 514/340
7,476,684 B2 * 1/2009 Minidis et al. .............. 514/340
7,585,881 B2 * 9/2009 Edwards et al. ............. 514/340

FOREIGN PATENT DOCUMENTS

| WO | WO-2006/014185 A1 | 2/2006 |
| WO | WO-2007/006530 A1 | 1/2007 |
| WO | WO-2007/040982 A1 | 4/2007 |
| WO | WO-2007/130824 A2 | 11/2007 |

OTHER PUBLICATIONS

Schoepp et al., "Metabotropic glutamate receptors in brain function and pathology", Jan. 1993 vol. 14, p. 13-20.
Schoepp, "Novel Functions for Subtypes of Metabotropic Glutamate Receptors", Neurochem. Int. vol. 24, No. 5, pp. 439-449 (1994).
Pin et al. "The Metabotropic Glutamate Receptors: Structure and Functions", Neuropharmacology vol. 34, No. 1 pp. 1-26, (1995).
Bordi and Ugolini, "Group I Metabotropic Glutamate Receptors: Implications for Brain Diseases", Progress in Neurobiology vol. 59, pp. 55-79 (1999).
Nakanishi, "Metabotropic Glutamate Receptors: Synaptic Transmission, Modulation, and Plasticity", Neuron, vol. 13, p. 1031-1037, Nov. 1994.
Knopfel et al., "Metabotrophic Glutamate Receptors: Novel Targets for Drug Development", vol. 38, p. 1417-1426 (1995).
Pin et al., "Alternative splicing generates metabotropic glutamate receptors inducing different patterns of calcium release in Xenopus oocytes", Proc. Natl. Acad. Sci. USA vol. 89, pp. 10331-10335, Nov. 1992.
Minakami et al., "Molecular Cloning and the Functional Expression of Two Isoforms of Human Metabotropic Glutamate Receptor Subtype 5", Biochemical and Biophysical Research Communications vol. 199, No. 3, 1994 pp. 1136-1143.
Joly et al., "Molecular, Functional, and Pharmacological Characterization of the Metabotropic Glutamate Receptor Type 5 Splice Variants: Comparison with mGluR1", The Journal of Neuroscience, May 1995 pp. 3970-3981.
Baskys, "Metabotropic receptors and 'slow' excitatory actions of glutamate agonists in the hippocampus", Neuroscience vol. 15, No. 3, 1992 pp. 92.
Watkins et al., "Phenylglycine derivatives as antagonists of metabotropic glutamate receptors", vol. 15, pp. 33-36 (1994).
Bashir et al., "Induction of LTP in the hippocampus needs synaptic activation of glutamate metabotropic receptors", Nature, vol. 363 (1993) pp. 347.
Bortolotto et al., "A molecular switch activated by metabotropic glutamate receptors regulates induction of long-term potentiation", Nature, vol. 368, pp. 740-743 (1994).
Aiba et al., "Reduced Hippocampal Long-Term Potentiation and Context-Specific Deficit in Associative Learning in mGluR1 Mutant Mice", Cell, vol. 79, pp. 365-375 (1994).

(Continued)

*Primary Examiner*—Golam M Shameem
(74) *Attorney, Agent, or Firm*—Birch, Stewart, Kolasch & Birch, LLP

(57) ABSTRACT

The present invention is directed to compounds of formula I:

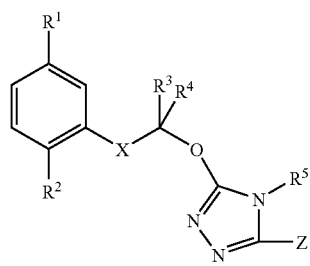

Wherein $R^1$ to $R^5$, X and Z are further defined in the description. The invention also relates to processes for the preparation of the compounds and to intermediates used in the preparation, pharmaceutical compositions containing the compounds, and to the use of the compounds in therapy.

6 Claims, No Drawings

OTHER PUBLICATIONS

Aiba et al., "Deficient Cerebellar Long-Term Depression and Impaired Motor Learning in mGluR1 Mutant Mice", Cell, vol. 79 pp. 377-388 (1994).

Meller et al., "Acute mechanical hyperalgesia is produced by coactivation of AMPA and metabotropic glutamate receptors", Neuroreport vol. 4, pp. 879-882 (1993).

Bordi and Ugolini, "Involvement of mGluR5 on acute nociceptive transmission", Brain Research, vol. 871, pp. 223-233 (2000).

Cunningham et al., "Excitatory Amino Acid Receptors: A Gallery of New Targets for Pharmacological Intervention", Life Sciences, vol. 54, pp. 135-148 (1993).

Hollmann et al., "Cloned Glutamate Receptors", Annu. Rev. Neuroscience vol. 17 pp. 31-108 (1994).

Spooren et al., "Novel allosteric antagonists shed light on mglu5 receptors and CNS disorders", TRENDS in Pharmacological Sciences vol. 22, pp. 331-337 (2001).

Gasparini et al., "Allosteric modulators of group I metabotropic glutamate receptors: novel subtype-selective ligands and therapeutic perspectives", Current Opinion in Pharmacology vol. 2, pp. 43-49 (2002).

Neugebauer, "Metabotropic glutamate receptors—important modulators of nociception and pain behavior", Pain vol. 98, pp. 1-8 (2002).

Holloway et al., "Pathophysiology of Gastroesophageal Reflux", Gastroenterology Clinics of North America vol. 19, pp. 517-535 (1990).

Miyaura et al., "The Palladium-Catalyzed Cross-Coupling Reaction of Phenylboronic Acid With Haloarenes in the Presence of Bases", Synthetic Communications, vol. 11 pp. 513-519 (1981).

Chiou et al., "A Simplified Procedure for Preparing 3,5-Disubstituted-1,2,4-Oxadiazoles by Reaction of Amidoximes with Acyl Chlorides in Pyridine Solution", J. Heterocyclic Chem. vol. 26 pp. 125 (1989).

\* cited by examiner

MGLUR5 MODULATORS

This Nonprovisional application claims priority under 35 U.S.C. §119(e) on U.S. Provisional Application No(s). 60/828,325 filed on Oct. 5, 2006, the entire contents of which are hereby incorporated by reference.

FIELD OF THE INVENTION

The present invention is directed to novel compounds, their use in therapy and pharmaceutical compositions comprising said novel compounds.

BACKGROUND OF THE INVENTION

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999).

Molecular cloning has identified eight distinct mGluR subtypes, termed mGluR1 through mGluR8. Nakanishi, *Neuron* 13:1031 (1994), Pin et al., *Neuropharmacology* 34:1 (1995), Knopfel et al., *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995).

Metabotropic glutamate receptor subtypes may be subdivided into three groups, Group 1, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Neurological, Psychiatric and Pain Disorders

Attempts at elucidating the physiological roles of Group I mGluRs suggest that activation of these receptors elicits neuronal excitation. Various studies have demonstrated that Group I mGluR agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1 (1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated, Meller et al., *Neuroreport* 4: 879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13: 1031 (1994), Pin et al., *Neuropharmacology* 34: 1, Knopfel et al., *J. Med. Chem.* 38:1417 (1995).

Further, Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease and pain. Schoepp et al., *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders.

Gastrointestinal Disorders

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. Holloway & Dent 1990 *Gastroenterol. Clin. N. Amer.* 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

The novel compounds according to the present invention are assumed to be useful for the inhibition of transient lower esophageal sphincter relaxations (TLESRs) and thus for treatment of gastro-esophageal reflux disorder (GERD).

It is well known that certain compounds may cause undesirable effects on cardiac repolarisation in man, observed as a prolongation of the QT interval on electrocardiograms (ECG). In extreme circumstances, this drug-induced prolongation of the QT interval can lead to a type of cardiac arrhythmia called Torsades de Pointes (TdP; Vandenberg et al. is hERG K+ channels: friend and foe. Trends Pharmacol Sci 2001; 22: 240-246), leading ultimately to ventricular fibrillation and sudden death. The primary event in this syndrome is inhibition of the rapid component of the delayed rectifying potassium current (IKr) by these compounds. The compounds bind to the aperture-forming alpha sub-units of the channel protein carrying this current—sub-units that are encoded by the human ether-a-go-go-related gene (hERG). Since IKr plays a key role in repolarisation of the cardiac action potential, its inhibition slows repolarisation and this is manifested as a prolongation of the QT interval. Whilst QT interval prolongation is not a safety concern per se, it carries a risk of cardiovascular adverse effects and in a small percentage of people it can lead to TdP and degeneration into ventricular fibrillation.

Generally, compounds of the present invention have low activity against the hERG-encoded potassium channel. In this regard, low activity against hERG in vitro is indicative of low activity in vivo.

It is also desirable for drugs to possess good metabolic stability in order to enhance drug efficacy. Stability against human microsomal metabolism in vitro is indicative of stability towards metabolism in vivo.

Because of their physiological and pathophysiological significance, there is a need for new potent mGluR agonists and antagonists that display a high selectivity for mGluR subtypes, particularly the Group I receptor subtype, most particularly the mGluR5.

The object of the present invention is to provide compounds exhibiting an activity at metabotropic glutamate receptors (mGluRs), especially at the mGluR5 receptor. In particular, the compounds according to the present invention are predominantly peripherally acting, i.e. have a limited ability of passing the blood-brain barrier.

SUMMARY OF THE INVENTION

The present invention relates to a compound of formula I:

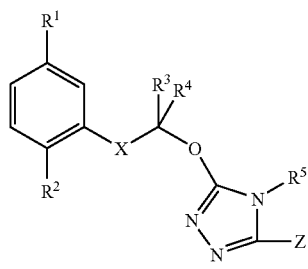

(I)

wherein
$R^1$ is selected from the group consisting of methyl, halogen and cyano;
$R^2$ is selected from the group consisting of hydrogen and fluoro;
$R^3$ is selected from the group consisting of hydrogen and $C_1$-$C_3$ alkyl;
$R^4$ is selected from the group consisting of hydrogen and $C_1$-$C_3$ alkyl;
$R^5$ is selected from the group consisting of $C_1$-$C_3$ alkyl and cyclopropyl;
X is selected from the group consisting of:

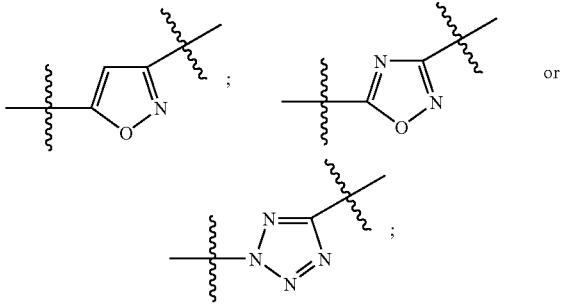

and Z is selected from the group consisting of:

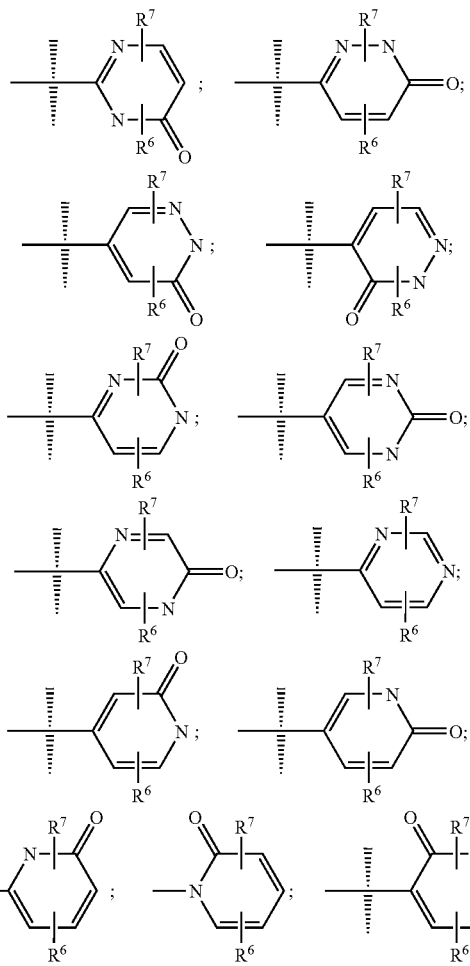

-continued

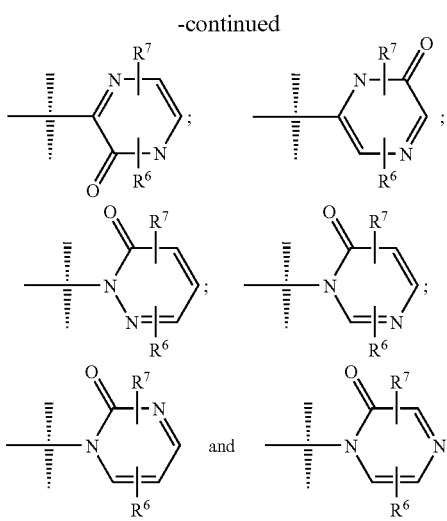

wherein

R⁶ is selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen;

R⁷ is selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen;

as well as pharmaceutically acceptable salts, hydrates, isoforms, tautomers and/or enantiomers thereof.

Another object of the invention is to provide a pharmaceutical composition comprising a compound according to formula I together with a pharmaceutically acceptable carrier or excipient.

Yet another object of the invention is a method for the treatment or prevention of neurological and psychiatric disorders associated with glutamate dysfunction in an animal in need of such treatment. The method comprises the step of administering to the animal a therapeutically effective amount of a compound of formula I or a pharmaceutical composition thereof. Preferably, the animal is a mammal; more preferably a human being.

Still another object of the invention is the use of a compound according to formula I, or a pharmaceutically acceptable salt or solvate thereof, for the manufacture of a medicament for the treatment of any of the conditions discussed herein.

Another object of the invention provides a compound of formula I, or a pharmaceutically acceptable salt or solvate thereof, for use in therapy.

The invention additionally provides processes for the preparation of compounds of formula I. General and specific processes are discussed in more detail below.

DETAILED DESCRIPTION

The present invention is based upon the discovery of compounds that exhibit activity as pharmaceuticals, in particular as modulators of metabotropic glutamate receptors. More particularly, the compounds of the present invention exhibit activity as potentiators of the mGluR5 receptor, and are useful in therapy, in particular for the treatment of neurological and psychiatric disorders associated with glutamate dysfunction.

DEFINITIONS

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09 and 9.04.

The term "alkyl" as used herein means a straight- or branched-chain hydrocarbon radical having from one to six carbon atoms, and includes methyl, ethyl, propyl, isopropyl, t-butyl and the like.

The term "cycloalkyl" as used herein means a cyclic group (which may be unsaturated) having from three to seven carbon atoms, and includes cyclopropyl, cyclohexyl, cyclohexenyl and the like.

The term "alkoxy" as used herein means a straight- or branched-chain alkoxy radical having from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "aryl" as used herein means an aromatic group having five to twelve atoms, and includes phenyl, naphthyl and the like.

The term "heteroaryl" means an aromatic group which includes at least one heteroatom selected from the group consisting of N, S and O, and includes groups and includes pyridyl, indolyl, furyl, benzofuryl, thienyl, benzothienyl, quinolyl, oxazolyl and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of formula I for laboratory use, or for subsequent conversion to a pharmaceutically acceptable acid addition salt.

A "pharmaceutically acceptable basic addition salt" is any non-toxic organic or inorganic base addition salt of the acid compounds represented by formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

The term "solvate" means a compound of formula I or the pharmaceutically acceptable salt of a compound of formula I wherein molecules of a suitable solvent are incorporated into a crystal lattice. A suitable solvent is physiologically tolerable at the dosage administered as the solvate. Examples of suitable solvents are ethanol, water and the like. When water is the solvent, the molecule is referred to as a hydrate.

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds

Compounds of the invention conform generally to formula I:

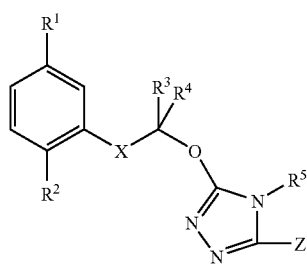

(I)

wherein $R^1$ is selected from the group consisting of methyl, halogen and cyano;

$R^2$ is selected from the group consisting of hydrogen and fluoro;

$R^3$ is selected from the group consisting of hydrogen and $C_1$-$C_3$ alkyl;

$R^4$ is selected from the group consisting of hydrogen and $C_1$-$C_3$ alkyl;

$R^5$ is selected from the group consisting of $C_1$-$C_3$ alkyl and cyclopropyl;

X is selected from the group consisting of:

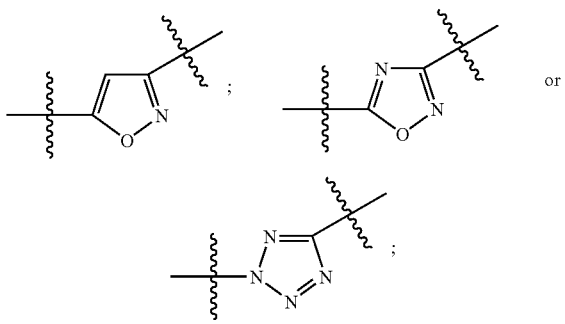

and Z is selected from the group consisting of:

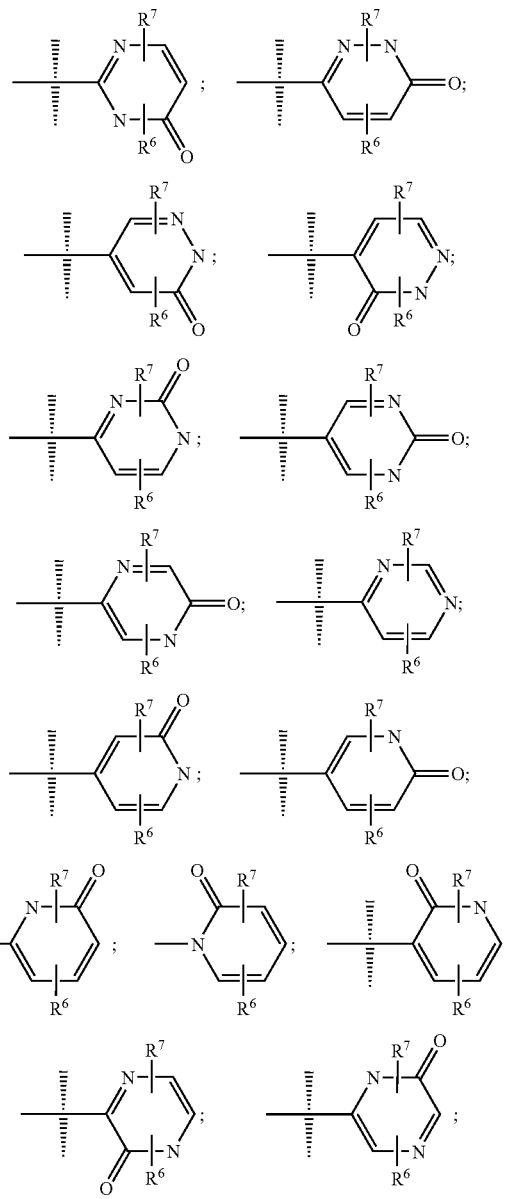

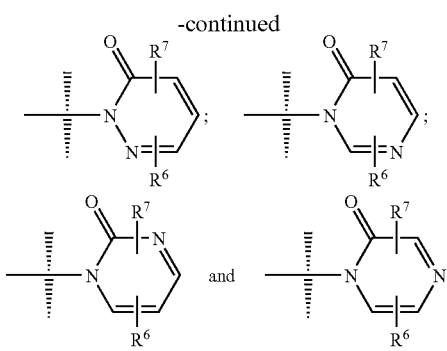

wherein

R[6] is selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen;

R[7] is selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen;

as well as pharmaceutically acceptable salts, hydrates, isoforms, tautomers and/or enantiomers thereof.

In particular embodiments R[1] is selected from the group consisting of chloro, cyano and methyl.

In a further embodiment, R[2] is hydrogen.

In a further embodiment, R[3] is methyl.

In a further embodiment, R[3] is $C_1$-$C_3$ alkyl and R[4] is hydrogen.

In a further embodiment, R[3] is $C_1$-$C_3$ alkyl and R[4] is $C_1$-$C_3$ alkyl.

In a further embodiment, R[4] is H.

In a further embodiment, R[5] is $C_1$-$C_3$ alkyl. In a further embodiment, R[5] is methyl.

In a further embodiment, R[6] is methyl. In a further embodiment, R[6] is hydrogen.

In a further embodiment, R[7] is hydrogen. In a further embodiment, R[7] is $C_1$-$C_3$ alkyl.

In a further embodiment, Z is

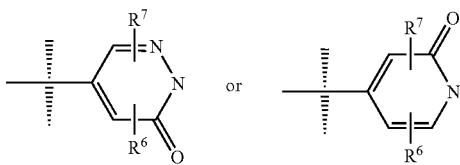

In formula I above, X may be present in any of the two possible orientations.

Another embodiment is a pharmaceutical composition comprising as active ingredient a therapeutically effective amount of the compound according to formula I, in association with one or more pharmaceutically acceptable diluents, excipients and/or inert carriers.

Other embodiments, as described in more detail below, relate to a compound according to formula I for use in therapy, in treatment of mGluR5 mediated disorders, in the manufacture of a medicament for the treatment of mGluR5 mediated disorders.

Still other embodiments relate to a method of treatment of mGluR5 mediated disorders, comprising administering to a mammal a therapeutically effective amount of the compound according to formula I.

In another embodiment, there is provided a method for inhibiting activation of mGluR5 receptors, comprising treating a cell containing said receptor with an effective amount of the compound according to formula I.

The compounds of the present invention are useful in therapy, in particular for the treatment of neurological, psychiatric, pain, and gastrointestinal disorders.

It will also be understood by those of skill in the art that certain compounds of the present invention may exist in solvated, for example hydrated, as well as unsolvated forms. It will further be understood that the present invention encompasses all such solvated forms of the compounds of formula I.

Within the scope of the invention are also salts of the compounds of formula I. Generally, pharmaceutically acceptable salts of compounds of the present invention are obtained using standard procedures well known in the art, for example, by reacting a sufficiently basic compound, for example an alkyl amine with a suitable acid, for example, HCl, acetic acid or a methanesulfonic acid to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the compounds 36.1 to 38.7, illustrated in the following table, their pharmaceutically acceptable salts, hydrates, solvates, optical isomers, and combinations thereof:

| Example No. | Structure | Name |
|---|---|---|
| 36.1 | 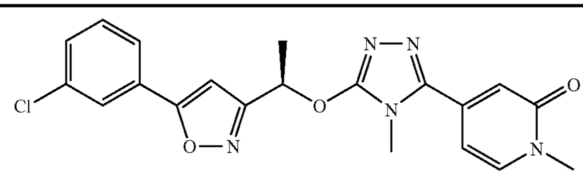 | 4-(5-{(1R)-1-[5-(3-Chlorophenyl)isoxazol-3-yl]ethoxy}-4-methyl-4H-1,2,4-triazol-3-yl)-1-methylpyridin-2(1H)-one |

-continued

| Example No. | Structure | Name |
|---|---|---|
| 36.2 | 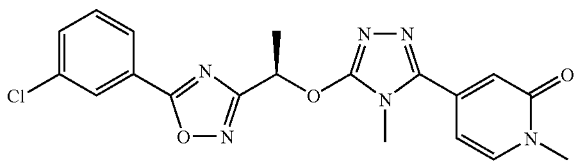 | 4-(5-{(1R)-1-[5-(3-Chlorophenyl)-1,2,4-oxadiazol-3-yl]ethoxy}-4-methyl-4H-1,2,4-triazol-3-yl)-1-methylpyridin-2(1H)-one |
| 37.1 | 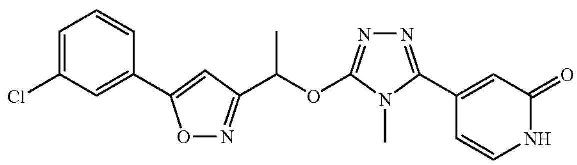 | 4-(5-{1-[5-(3-Chlorophenyl)isoxazol-3-yl]ethoxy}-4-methyl-4H-1,2,4-triazol-3-yl)pyridin-2(1H)-one |
| 37.2 | 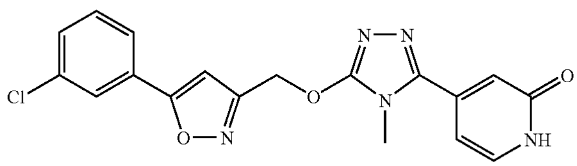 | 4-(5-{[5-(3-chlorophenyl)isoxazol-3-yl]methoxy}-4-methyl-4H-1,2,4-triazol-3-yl)pyridin-2(1H)-one |
| 37.3 | 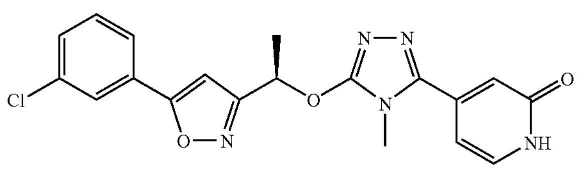 | 4-(5-{(1R)-1-[5-(3-Chlorophenyl)isoxazol-3-yl]ethoxy}-4-methyl-4H-1,2,4-triazol-3-yl)pyridin-2(1H)-one |
| 38.1 | 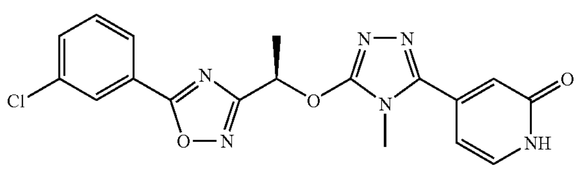 | 4-(5-{(1R)-1-[5-(3-Chlorophenyl)-1,2,4-oxadiazol-3-yl]ethoxy}-4-methyl-4H-1,2,4-triazol-3-yl)pyridin-2(1H)-one |
| 38.2 | 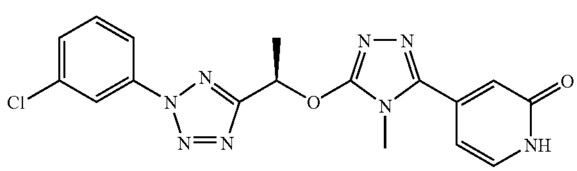 | 4-(5-{(1R)-1-[2-(3-Chlorophenyl)-2H-tetrazol-5-yl]ethoxy}-4-methyl-4H-1,2,4-triazol-3-yl)pyridin-2(1H)-one |
| 38.3 | 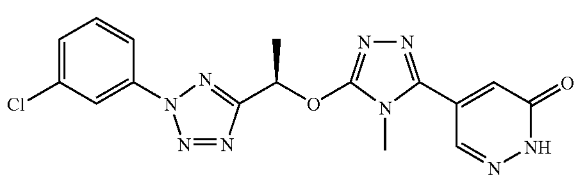 | 5-(5-{(1R)-1-[2-(3-Chlorophenyl)-2H-tetrazol-5-yl]ethoxy}-4-methyl-4H-1,2,4-triazol-3-yl)pyridazin-3(2H)-one |
| 38.4 | 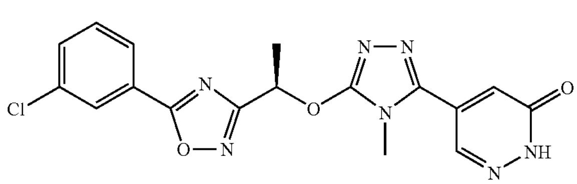 | 5-(5-{(1R)-1-[5-(3-Chlorophenyl)-1,2,4-oxadiazol-3-yl]ethoxy}-4-methyl-4H-1,2,4-triazol-3-yl)pyridazin-3(2H)-one |

-continued

| Example No. | Structure | Name |
|---|---|---|
| 38.5 | 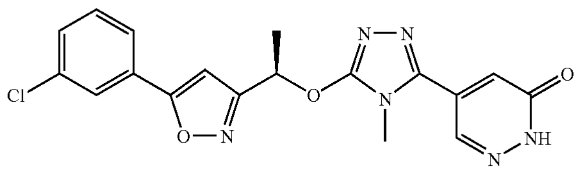 | 5-(5-{(1R)-1-[5-(3-Chlorophenyl)isoxazol-3-yl]ethoxy}-4-methyl-4H-1,2,4-triazol-3-yl)pyridazin-3(2H)-one |
| 38.6 | 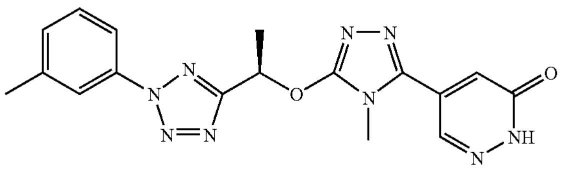 | 5-(4-Methyl-5-{(1R)-1-[2-(3-methylphenyl)-2H-tetrazol-5-yl]ethoxy}-4H-1,2,4-triazol-3-yl)pyridazin-3(2H)-one |
| 38.7 | 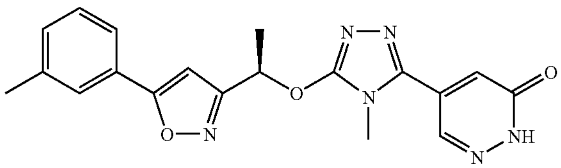 | 5-(4-Methyl-5-{(1R)-1-[5-(3-methylphenyl)isoxazol-3-yl]ethoxy}-4H-1,2,4-triazol-3-yl)pyridazin-3(2H)-one |

Pharmaceutical Composition

The compounds of the present invention may be formulated into conventional pharmaceutical compositions comprising a compound of formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, or from about 0.10% w to 50% w, of a compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

The compounds according to the present invention are useful in the treatment of conditions associated with excitatory activation of mGluR5 and for inhibiting neuronal damage caused by excitatory activation of mGluR5. The compounds may be used to produce an inhibitory effect of mGluR5 in mammals, including man.

The Group I mGluR receptors including mGluR5 are highly expressed in the central and peripheral nervous system and in other tissues. Thus, it is expected that the compounds of the invention are well suited for the treatment of mGluR5- mediated disorders such as acute and chronic neurological and psychiatric disorders, gastrointestinal disorders, and chronic and acute pain disorders.

The invention relates to compounds of formula I, as defined hereinbefore, for use in therapy.

The invention relates to compounds of formula I, as defined hereinbefore, for use in treatment of mGluR5-mediated disorders.

The invention relates to compounds of formula I, as defined hereinbefore, for use in treatment of Alzheimer's disease senile dementia, AIDS-induced dementia, Parkinson's disease, amyotrophic lateral sclerosis, Huntington's Chorea, migraine, epilepsy, schizophrenia, depression, anxiety, acute anxiety, opthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of formula I, as defined above, for use in treatment of pain related to migraine, inflammatory pain, neuropathic pain disorders such as diabetic neuropathies, arthritis and rheumatoid diseases, low back pain, post-operative pain and pain associated with various conditions including cancer, angina, renal or biliary colic, menstruation, migraine and gout.

The invention relates to compounds of formula I as defined hereinbefore, for use in treatment of stroke, head trauma, anoxic and ischemic injuries, hypoglycemia, cardiovascular diseases and epilepsy.

The present invention relates also to the use of a compound of formula I as defined hereinbefore, in the manufacture of a medicament for the treatment of mGluR Group I receptor-mediated disorders and any disorder listed above.

One embodiment of the invention relates to the use of a compound according to formula I in the treatment of gastrointestinal disorders.

Another embodiment of the invention relates to the use of a formula I compound for the manufacture of a medicament for inhibition of transient lower esophageal sphincter relaxations, for the treatment of GERD, for the prevention of gastroesophageal reflux, for the treatment regurgitation, for treatment of asthma, for treatment of laryngitis, for treatment of lung disease, for the management of failure to thrive, for the treatment of irritable bowel syndrome (IBS) and for the treatment of functional dyspepsia (FD).

Another embodiment of the present invention relates to the use of a compound of formula I for treatment of overactive bladder or urinary incontinence.

The wording "TLESR", transient lower esophageal sphincter relaxations, is herein defined in accordance with Mittal, R. K, Holloway, R. H., Penagini, R., Blackshaw, L. A., Dent, J, 1995; *Transient lower esophageal sphincter relaxation. Gastroenterology* 109, pp. 601-610.

The wording "reflux" is herein defined as fluid from the stomach being able to pass into the esophagus, since the mechanical barrier is temporarily lost at such times.

The wording "GERD", gastro-esophageal reflux disease, is herein defined in accordance with van Heerwarden, M. A., Smout A. J. P. M., 2000; *Diagnosis of reflux disease. Baillière's Clin. Gastroenterol.* 14, pp. 759-774.

The compounds of formula I above are useful for the treatment or prevention of obesity or overweight, (e.g., promotion of weight loss and maintenance of weight loss), prevention or reversal of weight gain (e.g., rebound, medication-induced or subsequent to cessation of smoking), for modulation of appetite and/or satiety, eating disorders (e.g. binge eating, anorexia, bulimia and compulsive) and cravings (for drugs, tobacco, alcohol, any appetizing macronutrients or non-essential food items).

The invention also provides a method of treatment of mGluR5-mediated disorders and any disorder listed above, in a patient suffering from, or at risk of, said condition, which comprises administering to the patient an effective amount of a compound of formula I, as hereinbefore defined.

The dose required for the therapeutic or preventive treatment of a particular disorder will necessarily be varied depending on the host treated, the route of administration and the severity of the illness being treated.

In the context of the present specification, the term "therapy" and "treatment" includes prevention or prophylaxis, unless there are specific indications to the contrary. The terms "therapeutic" and "therapeutically" should be construed accordingly.

In this specification, unless stated otherwise, the term "antagonist" and "inhibitor" shall mean a compound that by any means, partly or completely, blocks the transduction pathway leading to the production of a response by the ligand.

The term "disorder", unless stated otherwise, means any condition and disease associated with metabotropic glutamate receptor activity.

Non-Medical Use

In addition to their use in therapeutic medicine, the compounds of formula I, as well as salts and hydrates of such compounds, are useful as pharmacological tools in the development and standardization of in vitro and in vivo test systems for the evaluation of the effects of inhibitors of mGluR related activity in laboratory animals such as cats, dogs, rabbits, monkeys, rats and mice, as part of the search for new therapeutic agents.

Methods of Preparation

Another aspect of the present invention provides processes for preparing compounds of formula I, or salts or hydrates thereof. Processes for the preparation of the compounds in the present invention are described herein.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C.

The term "reflux" shall mean, unless otherwise stated, in reference to an employed solvent a temperature at or above the boiling point of named solvent.

Abbreviations
atm Atmosphere
aq. Aqueous
BINAP 2,2'-bis(diphenylphosphino)-1,1'-binaphthyl
Boc tert-butoxycarbonyl
CDI N,N'-Carbonyldiimidazole
DCC N,N-Dicyclohexylcarbodiimide
DCM Dichloromethane
DBU Diaza(1,3)bicyclo[5.4.0]undecane
DEA N,N-Diisopropyl ethylamine
DIBAL-H Diisobutylaluminium hydride
DIC N,N'-Diisopropylcarbodiimide
DMAP N,N-Dimethyl-4-aminopyridine
DMF Dimethylformamide
DMSO Dimethylsulfoxide
DPPF Diphenylphosphinoferrocene
EDCl N-[3-(Dimethylamino)propyl]-N'-ethylcarbodiimide hydrochloride
EDC 1-Ethyl-3-(3-dimethylaminopropyl)carbodiimide
$Et_2O$ Diethyl ether
EtOAc Ethyl acetate
EtOH Ethanol
EtI Iodoethane
Et Ethyl
Fmoc 9-fluorenylmethyloxycarbonyl
h hour(s)
HetAr Heteroaryl
HOBt N-Hydroxybenzotriazole
HBTU O-(Benzotriazol-1-yl)-N,N,N',N'-tetramethyluronium hexafluorophosphate
HPLC High performance liquid chromatography
LAH Lithium aluminium hydride
LCMS HPLC mass spec
MCPBA m-Chloroperbenzoic acid
MeCN Acetonitrile
MeOH Methanol
min Minutes
MeI Iodomethane
MeMgCl Methyl magnesium chloride
Me Methyl
n-BuLi 1-Butyllithium
NaOAc Sodium acetate
NMR Nuclear magnetic resonance
NMP N-Methyl pyrrolidinone
nBuLi 1-Butyl lithium
o.n. Over night
RT Room temperature
TEA Triethylamine
THF Tetrahydrofuran
nBu normal Butyl
OMs Mesylate or methane sulfonate ester
OTs Tosylate, toluene sulfonate or 4-methylbenzene sulfonate ester
PCC Pyridinium chlorochromate
PPTS Pyridinium p-toluenesulfonate
TBAF Tetrabutylammonium fluoride
TLC Thin Layer Chromatography
pTsOH p-Toluenesulfonic acid
SPE Solid phase extraction (usually containing silica gel for mini-chromatography)
sat. Saturated General syntheses of 1,2,4-oxadiazole compounds of formula I Scheme 1

LG = Leaving Group
R = group(s) from intermediate precursors
R' = groups as defined in formula I A compound of formula I, wherein X is a 1,2,4-oxadiazole (V) may be prepared through cyclization of a compound of formula IV, which in turn may be formed from a suitably activated compound of formula III with a compound of formula II.

Compounds of formula II may be prepared from a suitable nitrile, The compound of formula III may be activated in the following non-limiting ways: I) as the acid chloride formed from the acid using a suitable reagent such as oxalyl chloride or thionyl chloride; ii) as an anhydride or mixed anhydride formed from treatment with a reagent such as alkyl chloroformate; iii) using traditional methods to activate acids in amide coupling reactions such as EDCl with HOBt or uronium salts like HBTU; iv) as an alkyl ester when the hydroxyamidine is deprotonated using a strong base like sodium tert-butoxide or sodium hydride in a solvent such as ethanol or toluene at elevated temperatures 50-110° C.).

This transformation of compounds II and III into compounds of type V may be performed as two consecutive steps via an isolated intermediate of type IV, as described above, or the cyclization of the intermediate formed in situ may occur spontaneously during the ester formation. The formation of ester IV may be accomplished using an appropriate aprotic solvent such as dichloromethane, tetrahydrofuran, N,N-dimethylformamide or toluene, with optionally an appropriate organic base such as triethylamine, diisopropylethylamine and the like or an inorganic base such sodium bicarbonate or potassium carbonate. The cyclization of compounds of formula IV to form an oxadiazole may be carried out on the crude ester with evaporation and replacement of the solvent with a higher boiling solvent such as DMF or with aqueous extraction to provide a semi-purified material or with material purified by standard chromatographic methods. The cyclization may be accomplished by heating conventionally or by microwave irradiation (100-180° C.), in a suitable solvent such as pyridine or N,N-dimethylformamide or using a lower temperature method employing reagents like tetrabutylammonium fluoride in tetrahydrofuran or by any other suitable known literature method.

Further examples of the above described reactions can be found in Poulain et al., Tetrahedron Lett., 2001, 42, 1495-98, Ganglott et al., Tetrahedron Lett., 2001, 42, 1441-43, and Mathvink et al, Bioorg. Med. Chem. Lett. 1999, 9, 1869-74, which are hereby included as references.

Synthesis of Nitriles and Acids for Use in Preparation of Compounds of Formula I Aryl nitriles are available by a variety of methods including cyanation of an aryl halide or triflate under palladium or nickel catalysis using an appropriate cyanide source such as zinc cyanide in an appropriate solvent such as N,N-dimethylformamide. The corresponding acid is available from the nitrile by hydrolysis under either acidic or basic conditions in an appropriate solvent such as aqueous alcohols. Aryl acids are also available from a variety of other sources, including iodo- or bromo-lithium exchange followed by trapping with $CO_2$ to give directly the acid.

Carboxylic acids may be converted to primary amides using any compatible method to activate the acid, including via the acid chloride or mixed anhydride, followed by trapping with any source of ammonia, including ammonium chloride in the presence of a suitable base, ammonium hydroxide, methanolic ammonia or ammonia in an aprotic solvent such as dioxane. This amide intermediate may be converted to the nitrile using a variety of dehydration reagents such as oxalyl chloride or thionyl chloride. This reaction sequence to convert an acid into a nitrile may also be applied to non-aromatic acids, including suitably protected amino acid derivatives. A suitable protecting group for an amine, in an amino acid or in a remote position of any other acid starting material, may be any group which removes the basicity and nucleophilicity of the amine functionality, including such carbamate protecting group as Boc.

Some acids are more easily prepared taking advantage of commercially available analogs. For example, 6-methylpyridine-4-carboxylic acid is prepared by dechlorination of 2-chloro-6-methylpyridine-4-carboxylic acid. Certain types of substituted fluoro-benzonitriles and benzoic acids are available from bromo-difluoro-benzene via displacement of one fluoro group with a suitable nucleophile such as imidazole in the presence of a base such as potassium carbonate in a compatible solvent such as N,N-dimethylformamide at elevated temperatures (80-120° C.) for extended periods of time. The bromo group may subsequently be elaborated into the acid or nitrile as above.

1,3-Disubstituted and 1,3,5-trisubstituted benzoic acids and benzonitriles may be prepared by taking advantage of readily available substituted isophthalic acid derivatives. Monohydrolysis of the diester allows selective reaction of the acid with a variety of reagents, most typically activating agents such as thionyl chloride, oxalyl chloride or isobutyl chloroformate and the like. From the activated acid, a number of products are available. In addition to the primary amide used to form the nitrile by dehydration as mentioned above, reduction to the hydroxymethyl analog may be carried out on the mixed anhydride or acid chloride using a variety of reducing agents such as sodium borohydride in a compatible solvent such as tetrahydrofuran. The hydroxymethyl derivative may be further reduced to the methyl analog using catalytic hydrogenation with an appropriate source of catalyst such as palladium on carbon in an appropriate solvent such as ethanol. The hydroxymethyl group may also be used in any reaction suitable for benzylic alcohols such as acylation, alkylation, transformation to halogen and the like. Halomethylbenzoic acids of this type may also be obtained from bromination of the methyl derivative when not commercially available. Ethers obtained by alkylation of the hydroxymethyl derivatives may also be obtained from the halomethylaryl benzoate derivatives by reaction with the appropriate alcohol using an appropriate base such as potassium carbonate or sodium hydroxide in an appropriate solvent such as tetrahydrofuran or the alcohol. When other substituents are present, these may also be employed in standard transformation reactions. Treatment of anilines with acid and sodium nitrite may yield a diazonium salt, which may be transformed into a halide such as fluoride using tetrafluoroboric acid. Phenols react in the presence of a suitable base such as potassium carbonate with alkylating agents to form aromatic ethers.

Formation of Isoxazole Precursor of Compounds of Formula I

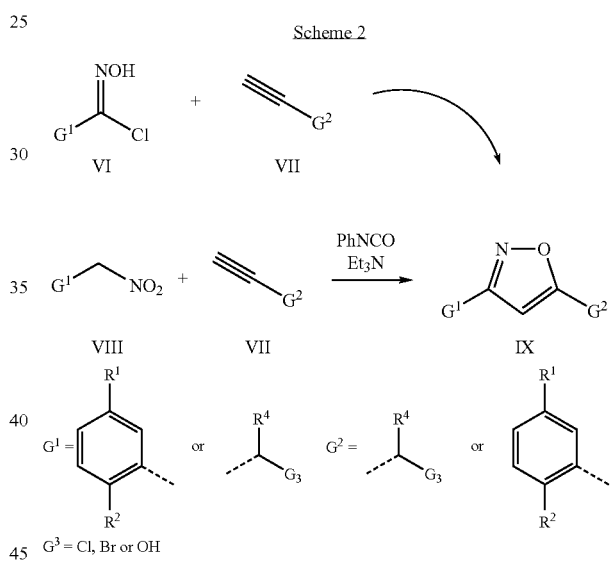

A compound of formula IX, wherein $G^1$ and/or $G^2$ is a moiety from an intermediate or group(s) as defined by formula I may be prepared by a 1,3-dipolar cycloaddition between compounds of formula VI and VII under basic conditions using a suitable base such as sodium bicarbonate or triethylamine at suitable temperatures (0° C.-100° C.) in solvents such as toluene. Synthesis of compounds of type VI has previously been described in the literature, e.g. Kim, Jae Nyoung; Ryu, Eung K; J. Org. Chem. 1992, 57, 6649-50. 1,3-Dipolar cycloaddition with acetylenes of type VII can also be effected using substituted nitromethanes of type VIII via activation with an electrophilic reagent such as PhNCO in the presence of a base such as triethylamine at elevated temperatures (50-100° C.). Li, C-S.; Lacasse, E.; Tetrahedron Lett. 2002 43; 3565-3568. Several compounds of type VII are commercially available, or may be synthesized by standard methods as known by one skilled in the art.

Scheme 3

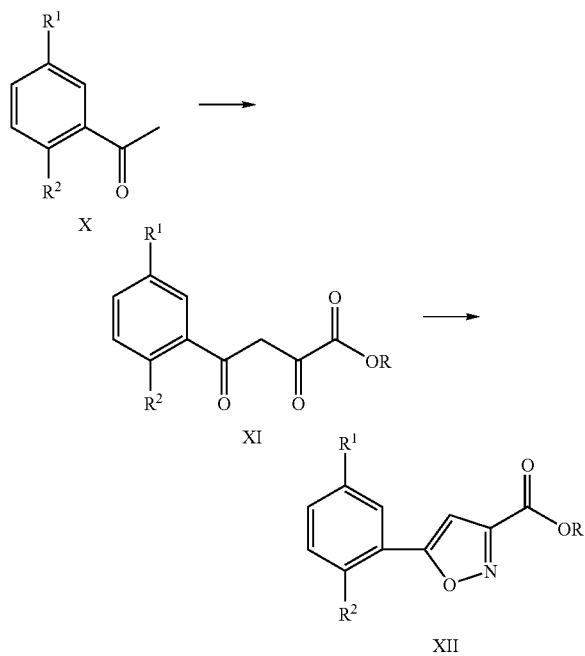

-continued

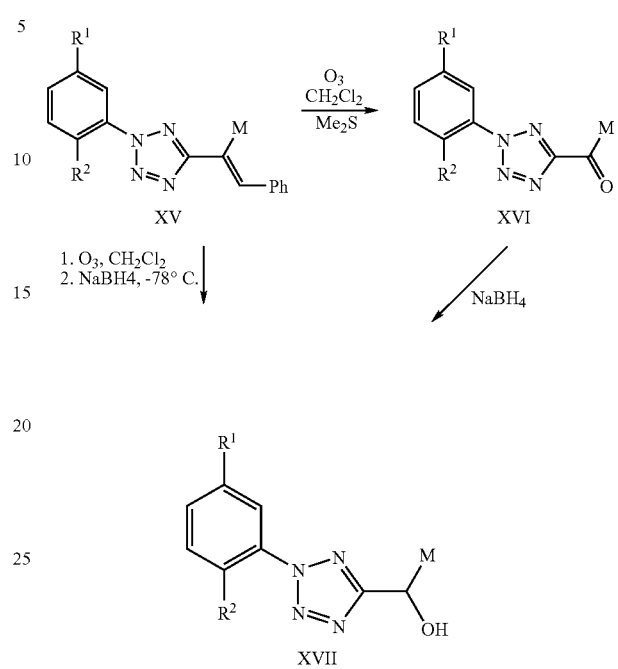

M = H or Me

Alternatively, compounds of formula I, which are available from a Claisen condensation of a methyl ketone X and an ester using basic conditions (see Scheme 3) using such bases as sodium hydride or potassium tert-butoxide, may yield compounds of formula XI via condensation and subsequent cyclization using hydroxylamine, for example in the form of the hydrochloric acid salt, at elevated temperatures (60-120° C.) to afford intermediate XII.

It is understood that for both methods, subsequent functional group transformations of intermediates such as IX and XII may be necessary. In the case of an ester group as in XII, these transformations may include, but is not limited to either of the following three procedures: a) Complete reduction using a suitable reducing agent such as LAH in solvents such as THF. b) Partial reduction using a suitable selective reducing agent such as DIBAL followed by addition of an alkylmetal reagent. c) Addition of an alkylmetal reagent such as an alkyl magnesium halide in solvents such as toluene or THF, followed by reduction with for example sodium borohydride in methanol.

Formation of Tetrazole Precursors of Compounds of Formula I

Scheme 4

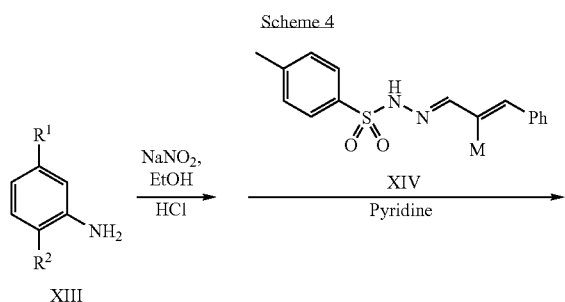

Compounds of formula I wherein X is tetrazole, as in intermediates XVI (M=H or Me) are prepared through condensation between arylsulphonylhydrazones XIV with diazonium salts derived from anilines XIII (Scheme 4). The tetrazole intermediate XV, obtained from the diazonium salt of XIII and the arylsulphonylhydrazones of cinnamaldehydes (M=H or Me) can be cleaved to provide an aldehyde (M=H) or ketone (M=Me) XV directly in a one-pot process using a reagent such as ozone or via the diol using a dihydroxylation reagent such as osmium tetroxide followed by subsequent cleavage using a reagent such as lead (IV) acetate. [J. Med. Chem. 2000, 43, 953-970].

The olefin can also be converted in one pot to the alcohol via ozonolysis followed by reduction with a reducing agent such as sodium borohydride. Aldehydes XV (M=H) may be reduced to primary alcohols of formula XVII (M=H) using well known reducing agents such as sodium or lithium borohydride, in a solvent such as methanol, THF or DMF at temperatures between 0-80° C. Secondary alcohols wherein M is not H may also be formed from aldehydes of formula XVI (M=H) via addition reactions of an organometallic reagent, for example Grignard reagents (e.g. MeMgX), in a solvent such as THF at temperatures between −78° C. to 80° C., and are typically performed between 0° C. and room temperature.

Scheme 5

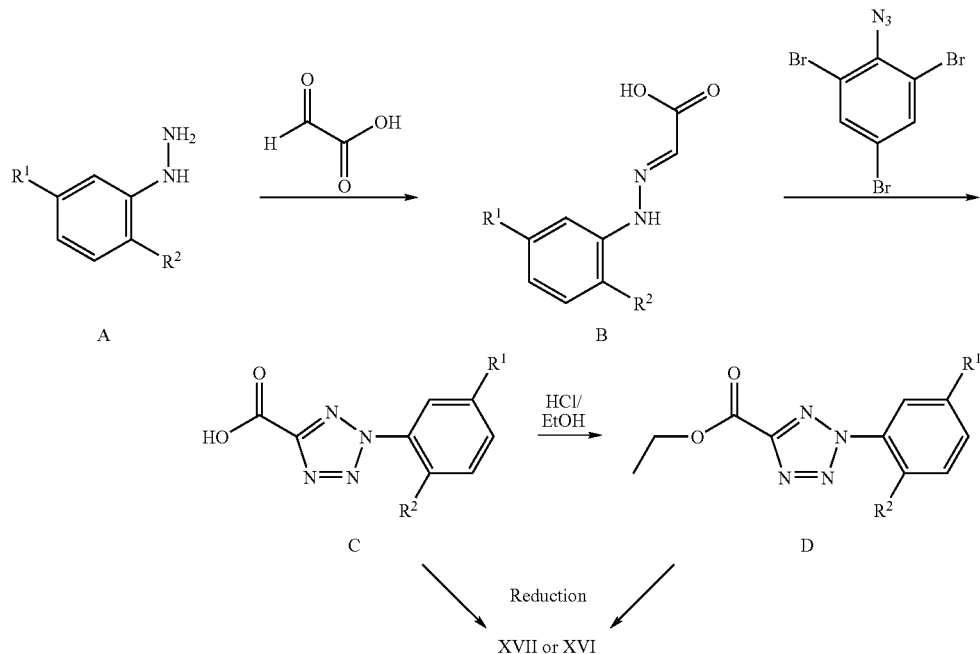

Alternatively, compounds of formula I wherein X is tetrazole, as in intermediates XVI (M=H) are prepared through condensation between arylhydrazines A with glyoxalic acid (Scheme 5). The intermediate B, obtained underwent to cycloaddition with azido 2,4,6-tribromobenzene to assemble the tetrazole core to give the carboxylic acid intermediate C. The acid C can either be reduced direct with $BH_3$ or $NaBH_4$/ $BF_3.Et_2O$ or transformed to the ester derivative D prior to reduction with $NaBH_4$ to provide alcohols of formula XVII (M=H). Partial reduction of D with for example Dibal-H could provide aldehydes which can be easily transformed into alcohols of formula XVII (M=H or Me). [*J. Med. Chem.* 1978, 21, 1254; *Heterocycles* 1995, 40, 583].

Preparation of Triazole Sulfone Intermediate

Compounds of formula XXIII containing the dihydro[1,2,4]triazole-3-thione ring may be prepared by initial N-acylation of a 4-alkylthiosemicarbazide of formula XIX using any suitable acylating agent of formula XVIII in a suitable solvent, for example pyridine DMF, DCM, THF, or acetonitrile at a temperature from −20 to 100° C. A pre-formed acylating agent such as an acid halide or ester may be employed, or an acid may be activated in situ by the treatment with standard activating reagents such as DCC, DIC, EDCl or HBTU, with or without the presence of co-reagents such as HOBt or DMAP. Formation of the acyclic intermediate XXII is followed by alkaline ring closure either spontaneously under the conditions of the acylation, or by heating at 50 to 150° C. in pyridine or in aqueous solvents in the presence of a base, such as NaOH, $NaHCO_3$ or $Na_2CO_3$, with or without co-solvents such as dioxane, THF, MeOH, EtOH or DMF. The acyclic intermediate XXII can also be formed by treatment of an acyl hydrazide of formula XX with a suitable isothiocyanate of formula XXI in a suitable solvent, for example 2-propanol, DCM, THF or the like at temperatures in the range of −20 to 120° C.

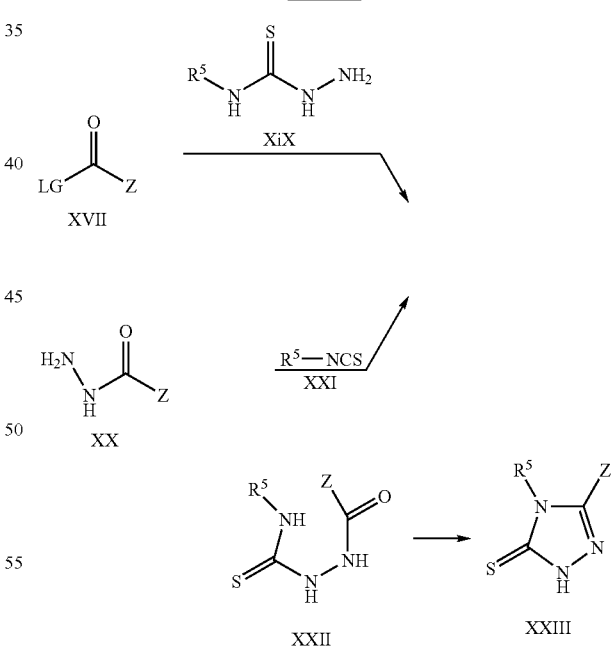

Scheme 6

Compounds of formula XXIII may then be converted to sulfones of formula XXV by initial alkylation of the sulphur atom to form intermediates of formula XXIV using primary alkyl halides such as MeI and EtI (alkyl is Me and Et respectively) in MeOH, EtOH, THF, acetone or the like at −30 to 100° C., followed by oxidation of intermediates XXIV using for example $KMnO_4$ in mixtures of water and acetic acid, or MCPBA in DCM, at −20 to 120° C., or by using any other suitable oxidant such as OXONE®.

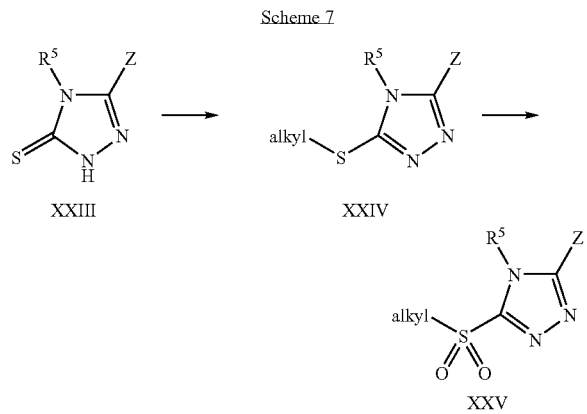

Scheme 7

Coupling of Alcohol to Sulfones

Compounds of formula I (wherein X as drawn in formula I is either tetrazole, oxadiazole or isoxazole) may be prepared by bond formation through nucleophilic replacement of a leaving group such as alk-SO$_2$ from compounds of formula XXV by an alcohol or alkoxide nucleophile under basic conditions. The base used may include strong hydridic bases, for example, NaH or milder bases, such as Cs$_2$CO$_3$, at temperatures from 0 to 80° C. in polar aprotic solvents such as DMF or acetonitrile. Other suitable leaving groups may include halogens, such as chloro or bromo.

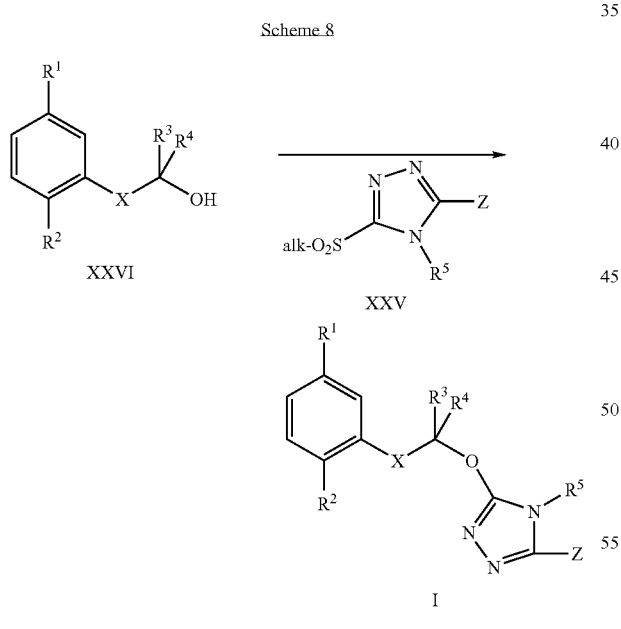

Scheme 8

In cases where Z contains an appropriate protecting group such as benzyl, methyl, t-Butyl or trialkylsilylethoxymethyl, various deprotection conditions included, hydrogenation under metal catalyzed conditions, acidic or Lewis acid mediated cleavage conditions (e.g. HBr/acetic acid or Dialkylaluminium chloride such as Me$_2$AlCl) or nucleophilic conditions (e.g. Et$_2$NCH$_2$CH$_2$SH.HCl, NaOtBu, DMF, reflux) may be used to obtain compounds of formula I.

Embodiments of the present invention will now be illustrated by the following non-limiting examples.

General Methods

All starting materials are commercially available or earlier described in the literature. The $^1$H and $^{13}$C NMR spectra were recorded on one of a Bruker 300 at 300 MHz Bruker, DPX400 at 400 MHz or Varian +400 spectrometer at 100 MHz, using TMS or the residual solvent signal as reference. NMR measurements were made on the delta scale (δ). Mass spectra were recorded on a QTOF Global Micromass or a Waters LCMS consisting of an Alliance 2795 (LC) and a ZQ single quadrupole mass spectrometer. The mass spectrometer was equipped with an electrospray ion source operated in a positive or negative ion mode. The ion spray voltage was ±3 kV and the mass spectrometer was scanned from m/z 100-700 with a scan time of 0.8 s. Column: X-Terra MS, Waters, C8, 2.1×50 mm, 3.5 μm and the column temperature was set to 40° C. A linear gradient was applied, run at 0% to 100% acetonitrile in 4 minutes, flow rate 0.3 mL/min. Mobile phase: acetonitrile/10 mM ammonium acetate in 5% acetonitrile in MilliQ Water. Preparative chromatography was run on a Gilson autopreparative HPLC with a diode array detector. Column: XTerra MS C8, 19×300 mm, 7 μm. Gradient with acetonitrile/0.1 M ammonium acetate in 5% acetonitrile in MilliQ Water, generally run from 20% to 60% acetonitrile, in 13 min. Flowrate: 20 mL/min. MS-triggered prep-LC was run on a Waters autopurification LC-MS system with a diode array detector and a ZQ mass detector. Column: XTerra MS C8, 19×100 mm, 5 μm. Gradient with acetonitrile/0.1 M ammonium acetate in 5% acetonitrile in MilliQ Water, run from 0% to 100% acetonitrile, in 10 min. Flowrate: 20 mL min. In some cases purification by a chromatotron was performed on rotating silica gel/gypsum (Merck, 60 PF-254 with calcium sulphate) coated glass sheets, with coating layer of 2 mm using a TC Research 7924T chromatotron. Alternatively Chem Elut Extraction Column (Varian, cat #1219-8002) and Mega BE-SI (Bond Elut Silica) SPE Columns (Varian, cat #12256018; 12256026; 12256034) were used during purification of the products.

Microwave heating was performed in a Smith Synthesizer Single-mode microwave cavity producing continuous irradiation at 2450 MHz (Personal Chemistry AB, Uppsala, Sweden).

Example 1

N',2-dihydroxypropanimidamide

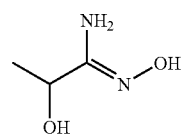

Hydroxylamine hydrochloride, 44 g (0.64 mol) and 25.5 g (0.64 mol) sodium hydroxide were dissolved in ethanol (500 mL) at RT and stirred for 3 h. After filtration, 8.1 g (0.11 mol) 2-hydroxypropanenitrile were added to the filtrate, followed by stirring for 4 h. After concentration to dryness the subtitle compound was obtained which was directly used in the next step.

$^1$H NMR (300 MHz, DMSO-d6) δ 8.88 (s, 1H), 5.15 (s, 1H), 5.02 (s, 1H), 4.00 (q, 1H), 1.19 (d, 3H).

Example 2

1-[5-(3-chlorophenyl)-1,2,4-oxadiazol-3-yl]ethanol

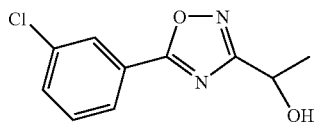

The title compound from Example 1 (6.45 g) was cooled on an ice-bath with 23.5 mL DEA in THF (200 mL). To this slurry 21.94 g 3-chlorobenzoyl chloride was added. The mixture was warmed to r.t. and stirred for 2 h. Addition of Et$_2$O (200 mL), washing with sat. aq. NH$_4$Cl and re-extraction of the aq. layer gave after combining and concentration of the org. layers followed by drying in vacuo 27.24 g, which was directly used in the next step. The material was dissolved in ethanol (250 mL) and refluxed for 1 h, followed by addition of 14.0 g (170 mmol) sodium acetate in water (40 mL). After refluxing over night, cooling to RT and addition of water (250 mL) the mixture was concentrated in vacuo to about half of its volume, resulting in a precipitate which was filtered off and recrystallized from EtOAc/heptane to yield 6.45 g (25%) of the title compound.

$^1$H NMR (300 MHz, CDCl$_3$) δ 8.14 (s, 1H), 8.02 (d, 1H), 7.57 (d, 1H), 7.47 (t, 1H), 5.04-5.14 (m, 1H), 2.51 (d, 1H), 1.67 (d, 3H).

Example 3.1

4-(3-Chloro-phenyl)-2,4-dioxo-butyric acid ethyl ester

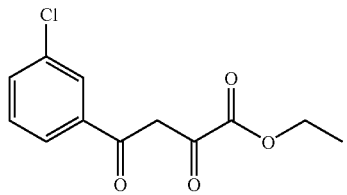

Sodium hydride (60% oil dispersion, 1.24 g, 31.1 mmol) was added in portions to a solution of 3-chloroacetophenone (4.0 g, 26 mmol) and diethyl oxalate (4.54 g, 31.1 mmol) in DMF (32 mL) at 0° C. The mixture stirred at room temperature for 1 hour and was then heated at 80° C. for a half an hour. After cooling, the mixture was treated with 3 M HCl and then diluted with ethyl acetate. The organic layer was washed with water (three times) and saturated brine, dried over anhydrous sodium sulfate, filtered and concentrated. The resulting residue was then purified by flash column chromatography on silica using 0-10% ethyl acetate in hexanes to afford of the title compound (4.43 g, 67%, yellow solid).

$^1$H NMR (300 MHz, CDCl$_3$) δ 15.12 (br s, 1H), 7.98 (s, 1H), 7.88 (d, 1H), 7.58 (d, 1H), 7.47 (t, 1H), 7.05 (s, 1H), 4.39 (m, 2H), 1.41 (m, 3H).

The examples below were prepared according to the above procedure:

| Example | Structure | Name | Yield |
| --- | --- | --- | --- |
| 3.2 | ![structure] | 2,4-Dioxo-4-m-tolyl-butyric acid methyl ester | 81%<br>6.61 g<br>Yellow solid |
| | $^1$H NMR (300 MHz, CDCl$_3$) δ 15.12 (br s, 1H), 7.81 (m, 2H), 7.43 (m, 2H), 7.15 (s, 1H), 3.91 (s, 3H), 2.46 (s, 3H) | | |
| 3.3 | ![structure] | 4-(3-Iodo-phenyl)-2,4-dioxo-butyric acid ethyl ester | 71%<br>24.2 g<br>Yellow solid |
| | $^1$H NMR (300 MHz, CDCl$_3$) δ 15.01 (broad s, 1H), 8.34 (d, 1H), 7.95 (m, 2H), 7.28 (s, 1H), 7.25 (m, 1H), 3.98 (s, 3H). | | |

Example 4.1

5-(3-Chloro-phenyl)-isoxazole-3-carboxylic acid ethyl ester

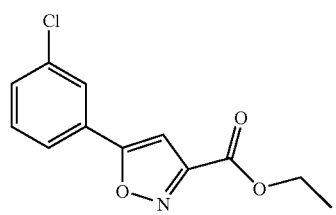

A solution of the title compound of Example 3.1 (3.00 g, 11.8 mmol) and hydroxylamine hydrochloride (2.46 g, 35.4 mmol) in methanol (60 mL) was heated at 80° C. for 4 hours. After cooling, the mixture was filtered and washed with cold methanol to afford the title compound in mixture with the methyl ester analog (2.0 g, 71%, white solid).

$^1$H NMR (300 MHz, CDCl$_3$) δ 7.82 (s, 1H), 7.72 (m, 1H), 7.47 (m, 2H), 4.03 (s, 3H).

The examples below were prepared according to the above procedure:

Example 4.4

Alternative synthesis of 5-(3-Methyl-phenyl)-isoxazole-3-carboxylic acid ethyl ester

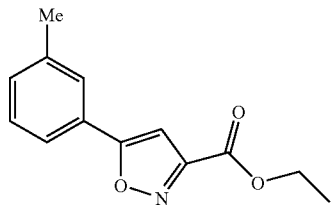

A solution of the title compound of Example 4.3 (3.0 g, 8.7 mmol) in THF (50 mL) was added Pd (PPh$_3$)$_2$Cl$_2$ (614 mg, 0.87 mmol) and then Me$_2$Zn (4.8 ml, 2M soln in toluene, 9.6 mmol) and the mixture was stirred at room temperature for 2 hours. The mixture concentrated under vacuum, diluted with CH$_2$Cl$_2$ and HCl (7.2 mL of 3 M HCl in 20 mls of water). The mixture was extracted with CH$_2$Cl$_2$, dried over Na$_2$SO$_4$ (anhydrous) and the solvent removed. The resulting residue was then purified by flash column chromatography using 1-9% ethyl acetate in hexane to afford the title compound (1.27 g, 63%, white solid).

| Example | Structure | Name | Yield |
|---------|-----------|------|-------|
| 4.2 | 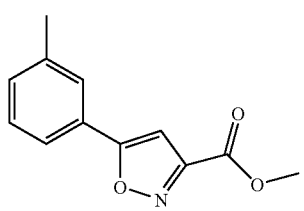 $^1$H NMR (300 MHz, CDCl$_3$) δ 7.63 (s, 1H), 7.60 (d, 1H), 7.38 (t, 1H), 7.29 (d, 1H), 6.92 (s, 1H), 4.01 (s, 3H), 2.43 (s, 3H) | 5-m-Tolyl-isoxazole-3-carboxylic acid methyl ester | 100% 6.51 g White solid |
| 4.3 | 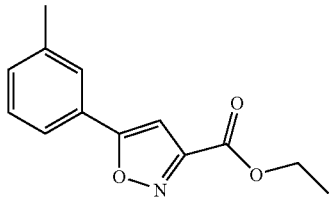 $^1$H NMR (300 MHz, CDCl$_3$) δ 8.18 (m, 1H), 7.82 (t, 2H), 7.26 (t, 1H), 6.97 (s, 1H), 4.03 (s, 3H). | 5-(3-Iodo-phenyl)-isoxazole-3-carboxylic acid ethyl ester | 72% 24.1 g Brown solid |

$^1$H NMR (300 MHz, CDCl$_3$) δ 7.64 (s, 1H), 7.61 (d, 1H), 7.39 (t, 1H), 7.29 (d, 1H), 6.92 (s, 1H), 4.48 (q, 2H), 2.44 (s, 3H), 1.46 (t, 3H),

Example 5.1

[5-(3-Chloro-phenyl)-isoxazol-3-yl]-methanol

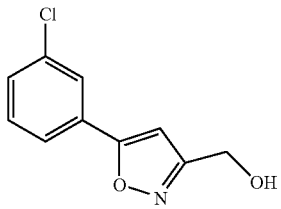

Lithium aluminum hydride (320 mg, 8.4 mmol) was slowly added to a solution of the mixture obtained in Example 4.1 (2.0 g, 8.4 mmol) in THF (100 mL) at room temperature. After 1 hour, the reaction mixture was quenched with water and then extracted with ethyl acetate. The organic layer was washed with water and saturated brine, dried over anhydrous sodium sulfate, filtered, and concentrated. The resulting residue was then purified by flash column chromatography using 15-40% ethyl acetate in hexane to afford the title compound (1.32 g, 75%, yellow solid).
$^1$H NMR (300 MHz, CDCl$_3$) δ 7.78 (s, 1H), 7.68 (m, 1H), 7.43 (m, 2H), 6.63 (s, 1H), 4.84 (d, 2H), 2.23 (t, 1H).

The example below was prepared according to the above procedure:

| Example | Structure | Name | Yield |
|---|---|---|---|
| 5.2 | 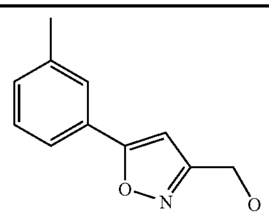 | (5-m-Tolyl-isoxazol-3-yl)-methanol | 92% 0.96 g Yellow oil |
| $^1$H NMR | (300 MHz, CDCl$_3$) δ 7.78 (s, 1 H), 7.76 (d, 1 H), 7.36 (t, 1 H), 7.25 (d, 1 H), 6.58 (s, 1 H), 4.83 (s, 2 H), 2.43 (s, 3 H), 2.08 (br, 1 H). | | |

Example 5.3

5-m-Tolyl-isoxazole-3-carbaldehyde

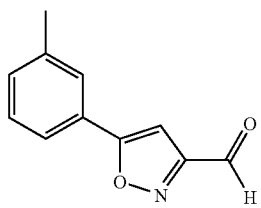

The crude product of the title compound from Example 5.2 (960 mg, 5 mmol) in CH$_2$Cl$_2$ was added PCC (1.6 g, 7.6 mmol) and the reaction was allowed to stir at room temperature overnight. The reaction was filtered and the filtrate was adsorbed onto silica. The crude product was purified by column chromatography (5-8% EtOAc/hexanes) to yield the pure product as a white solid (739 mg, 77%).
$^1$H NMR (300 MHz, CDCl$_3$) δ 10.20 (s, 1H), 7.84 (s, 1H), 7.83 (d, 1H), 7.41 (t, 1H), 7.32 (d, 1H), 6.89 (s, 1H), 2.45 (s, 3H).

The example below was prepared according to the above procedure:

| Example | Structure | Name | Yield |
|---|---|---|---|
| 5.4 | 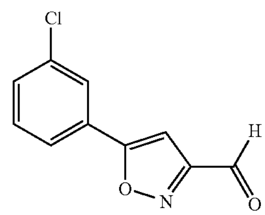 | 5-(3-Chloro-phenyl)-isoxazole-3-carbaldehyde | 49%; 0.80 g White solid |
| $^1$H NMR | (300 MHz, CDCl$_3$) δ 10.21 (s, 1 H), 7.84 (s, 1 H), 7.73 (d, 1 H), 7.48 (m, 2 H), 6.94 (s, 1 H). | | |

Example 6.1

1-[5-(3-Chloro-phenyl)-isoxazol-3-yl]-ethanone

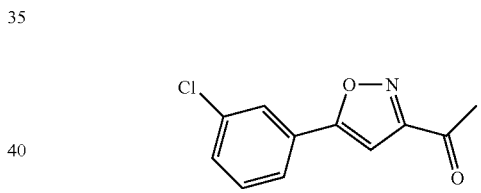

In a screw cap vial equipped with stir bar was added methyl magnesium iodide (3 M in diethyl ether) (0.79 mL, 2.38 mmol), toluene (1 mL), tetrahydrofuran (0.39 mL, 4.77 mmol) and triethylamine (1 mL, 7.15 mmol). The solution was cooled to 0° C. and to it added solution of the title compound of Example 4.1 (300 mg, 1.19 mmol) in toluene (5 mL). The resulting mixture was stirred at 0° C. for 5 h. The reaction mixture was quenched with 1 M hydrochloric acid (aqueous, 6.5 mL, 6.5 mmol), diluted with toluene (35 mL), sequentially washed with water (50 mL), saturated sodium bicarbonate (aqueous, 30 mL), water (50 mL) and brine (30 mL). The organic phase was concentrated, in vacuo. The isolated residue was dissolved in methanol (8 mL) and 20% potassium hydroxide (aqueous, 1 mL). The mixture was stirred at 45° C. for 30 minutes. At this point the mixture was concentrated, in vacuo. The isolated residue was dissolved in toluene (60 mL), sequentially washed with water (50 mL), saturated sodium bicarbonate (aqueous, 50 mL) and water (50 mL). The organic phase was concentrated, in vacuo. The crude residue was purified on silica gel using 2% ethyl acetate in hexanes to isolate the title compound as a white solid (156 mg, 60%).

¹H NMR (300 MHz, CDCl₃) δ 7.77 (m, 1H), 7.66 (m, 1H), 7.42 (m, 2H), 6.90 (s, 1H), 2.69 (s, 3H).

Example 7.1

1-[5-(3-Chloro-phenyl)-isoxazol-3-yl]-ethanol

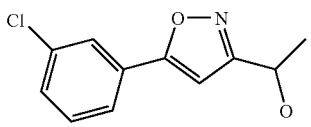

In a screw cap vial equipped with stir bar added the title compound of Example 6.1 (100 mg, 0.45 mmol), sodium borohydride (34 mg, 0.90 mmol) and methanol (3 mL). The resulting mixture was stirred at room temperature for 3 h. The reaction was quenched with water (30 mL) and brine (30 mL), extracted with dichloromethane (3 times 30 mL). The combined organic phase was dried (sodium sulfate), filtered and concentrated, in vacuo to isolate the title compound as a white solid (110 mg).
¹H NMR (300 MHz, CDCl₃) δ (ppm) 7.69 (m, 1H), 7.59 (m, 1H), 7.37 (m, 2H), 6.59 (s, 1H), 5.07 (q, 1H), 3.45 (bs, 1H), 1.58 (d, 3H).

Example 8.1

1-[5-(3-Methyl-phenyl)-isoxazol-3-yl]-ethanol

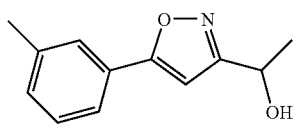

The title compound of Example 5.3 (739 mg, 3.9 mmol) was dissolved in THF (20 mL) under Argon and the flask was immersed in ice. Methyl magnesium bromide (1 M solution/diethyl ether 6.6 mL, 19.7 mmol) was added dropwise while the reaction was cooled in ice. After fifteen minutes at 0° C., the ice bath was removed and the reaction was allowed to stir at room temperature for two hours. Aqueous NH₄Cl (saturated) was added to quench the reaction and an aqueous workup was done extracting with ethyl acetate three times. The combined organic layers were washed with brine, dried over sodium sulfate, filtered and concentrated. The crude product was purified by column chromatography (3% MeOH/DCM) to yield the title compound as a clear oil (818 mg, 100%).
¹H NMR (300 MHz, CDCl₃) δ 7.60 (s, 1H), 7.58 (d, 1H), 7.35 (t, 1H), 7.27 (d, 1H), 6.56 (s, 1H), 5.10 (dq, 1H), 2.43 (s, 3H), 2.28 (d, 1H, OH), 1.60 (d, 3H).

Example 9.1

Cinnamaldehyde tosyl hydrazone

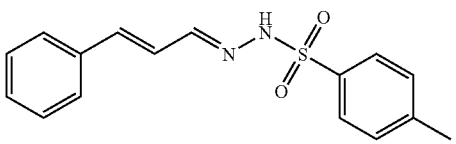

Cinnamaldehyde (8.80 g, 66.6 mmol) was added to p-toluene sulfonamide (12.44 g, 66.79 mmol) in ethanol (70 mL). The reaction immediately turned solid and ethanol (20 mL) was again added. The reaction was allowed to stir at room temperature for one hour and was then filtered. The solid was washed with methanol and dried by reduced pressure to yield the title compound as a white solid (17.5 g, 87%).
¹H NMR (300 MHz, CDCl₃) δ 8.23 (s, 1H), 7.88 (d, 2H), 7.60 (d, 1H), 7.34 (m, 6H), 6.83 (m, 2H), 2.43 (s, 3H).

Example 9.2

2-Methyl Cinnamaldehyde tosyl hydrazone

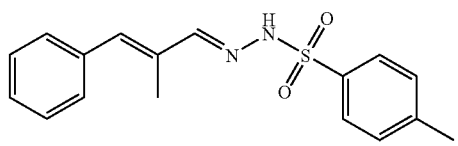

2-Methyl-3-phenylacrylaldehyde (15.0 g, 103 mmol) was added to p-toluene sulfonamide (19.2 g, 103 mmol) in ethanol (70 mL). The reaction immediately turned solid and ethanol (20 mL) was again added. The reaction was allowed to stir at room temperature for 8 h and was then filtered. The solid was washed with methanol and dried by reduced pressure to yield the title compound as a white solid (30.94 g, 96%).
¹H NMR (300 MHz, CD₃OD) δ 7.80 (d, 2H), 7.60 (s, 1H), 7.35 (m, 6H), 7.26 (m, 1H), 6.67 (s, 1H), 2.42 (s, 3H), 2.01 (s, 3H).

Example 10.1

3-(3-Chloro-phenyl)-5-styryl-2H-tetrazole

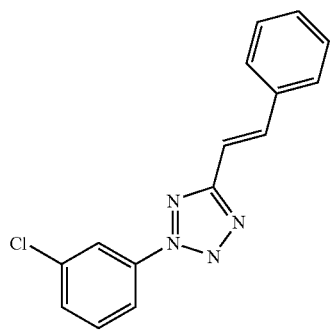

An aqueous (5 mL) solution of sodium nitrite (540.9 mg, 7.839 mmol) was added to a solution of 3-chloroaniline in water (7 mL), concentrated hydrochloric acid (3 mL) and ethanol (7 mL) via dropping funnel. The reaction was allowed to stir at 0° C. for ten minutes. This solution was poured into a dropping funnel and ice was added. This was added dropwise to a solution of the product obtained in example 9.1 (2.3 g, 7.7 mmol) in pyridine (20 mL). This was allowed to stir overnight. An aqueous workup was done extracting with DCM three times. The combined layers were washed with brine, dried over sodium sulfate, filtered and concentrated. The crude product was purified by column chromatography (20% EtOAc/hexanes) to yield the title compound as a light purple solid (433 mg, 19%).
¹H NMR (300 MHz, CDCl₃) δ 8.21 (m, 1H), 8.09 (dt, 1H), 7.89 (d, 1H), 7.61 (m, 2H), 7.49 (m, 5H), 7.24 (d, 1H).

Example 10.2

2-(3-Chlorophenyl)-5-[(E)-1-methyl-2-phenylvinyl]-2H-tetrazole

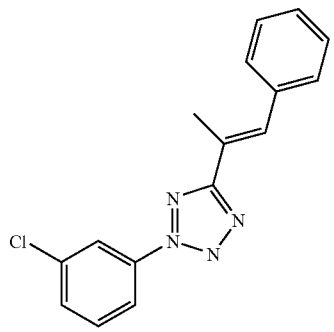

An aqueous (5 mL) solution of sodium nitrite (654 mg, 9.5 mmol) was added to a solution of 3-chloroaniline (0.92 mL, 8.7 mmol) in water (10 mL), concentrated hydrochloric acid (11.9 mL) and ethanol (7 mL) via dropping funnel. The reaction was allowed to stir at 0° C. for ten minutes. This solution was poured into a dropping funnel and ice was added. This was added dropwise to a solution of the title product of example 9.2 (2.5 g, 7.9 mmol) in pyridine (10 mL). This was allowed to stir at 0° C. for 1.5 h. The mixture was extracted with dichloromethane three times. The combined layers were washed with brine, dried over sodium sulfate, filtered and concentrated. The crude product was purified by column chromatography (20% EtOAc/hexanes) to yield the title compound as a red solid (736 mg, 28%).

$^1$H NMR (300 MHz, CDCl$_3$) δ) 8.23 (s, 1H), 8.11 (dd, 1H), 7.94 (s, 1H), 7.55-7.30 (m, 7H), 2.50 (d, 3H).

Example 11

General Procedure for Ozonolysis of the Phenyl Tetrazole Intermediates Followed by Aldehyde/Ketone Reduction with Sodium Borohydride The phenyl tetrazoles of Examples 9.1 or 10.1 were dissolved in dichloromethane and cooled to −78° C. Ozone was bubbled through the solution for a period of 10-30 minutes. The progress of the reaction was checked using a 10% EtOAc: Hexane TLC solvent system. Once the reaction appeared complete, sodium borohydride (70 mg/mmol tetrazole) and MeOH (~5 mL/mmol) were added to the solution. The solution was allowed to equilibrate back to room temperature and left overnight. Water (5 mL) and saturated ammonium chloride (5 mL) were added to the solution. The mixture was concentrated under low pressure and an aqueous workup was performed using DCM, water and brine. Anhydrous sodium sulfate was used to dry the solution. A standard flash column was run using a 10%-35% EtOAc:hexanes gradient solvent system. The samples were subjected to NMR analysis. The following table represents all the reactions performed.

The examples below were prepared according to the above procedure:

| Example | Structure | Name | Yield |
|---|---|---|---|
| 11.1 | 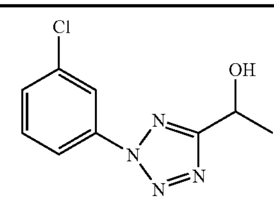 | 1-[2-(3-Chloro-phenyl)-2H-tetrazol-5-yl]-ethanol | 60% 1.01 g Orange Powder |
| $^1$H NMR | (300 MHz, CDCl$_3$) δ 8.18 (s, 1 H), 8.06 (d, 1 H), 7.51 (br, 2 H), 5.32 (br, 1 H), 2.70 (br, 1 H), 1.78 (d, 3 H) | | |
| 11.2 | 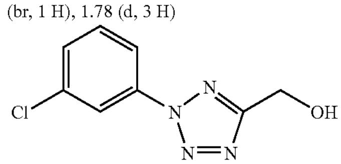 | 2-(3-Chloro-phenyl)-2H-tetrazol-5-yl]-methanol | 31% 460 mg Orange Solid |
| $^1$H NMR | (300 MHz, CDCl$_3$) δ 8.19 (s, 1 H), 8.06 (m, 1 H), 7.52 (m, 2 H), 5.08 (d, 2 H), 2.37 (t, 1 H) | | |

Preparation of Example 11.1 from Example 14.1:

The title compound of Example 14.1 (75.6 mg, 0.362 mmol) was dissolved in THF (2 mL) under Argon and the flask was immersed in ice. Methyl magnesium bromide (1 M solution/butyl ether 0.51 mL, 0.51 mmol) was added dropwise while the reaction was cooled in ice. After fifteen minutes at 0° C., the ice bath was removed and the reaction was allowed to stir at room temperature for two hours. Hydrochloric acid (1 M) was added to quench the reaction and an aqueous workup was done extracting with ethyl acetate three times. The combined organic layers were washed with brine, dried over sodium sulfate, filtered and concentrated. The crude product was purified by column chromatography (3% MeOH/DCM) to yield the title compound as a clear oil (62.4 mg, 77%).

Example 12.1

1-[2-(3-Chloro-phenyl)-2H-tetrazol-5-yl]-ethanone

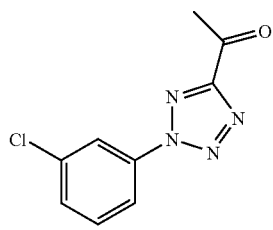

The title compound of Example 10.1 (1.50 g, 5.06 mmol) was dissolved in dichloromethane (79 mL) and ozone was bubbled through the solution for a period of 15 minutes. The solution turned from orange to a darker orange colour. The reaction completeness was checked using a 10% EtOAc: hexanes TLC solvent system. Oxygen was bubbled through the solution for an additional 5 minutes to remove any excess ozone remaining. Dimethyl sulfide (5 mL) was added to the solution and the mixture was allowed to equilibrate to room temperature. The solvent was removed under vacuum and an oily brown substance remained. A 3 cm flash column was prepared containing 15 cm silica and ~3 cm sand. The column was run using a 5% EtOAc:hexanes solvent system. The eluted fractions containing the product were collected and concentrated under low pressure. Flash column chromatography (silica, 5% EtOAc:hexanes) yielded 893 mg (79.4% yield) of the title compound.

$^1$H NMR (300 MHz, CDCl$_3$) δ 8.22 (s, 1H), 8.11 (m, 1H), 7.54 (d, 1H), 2.85 (s, 3H).

Example 13.1

1-[2-(3-Chloro-phenyl)-2H-tetrazol-5-yl]-2-phenyl-ethane-1,2-diol

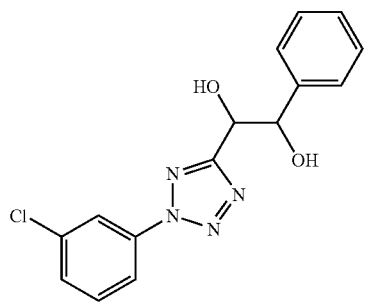

The title compound of Example 9.1 (127 mg, 0.446 mmol) was weighed into a vial and citric acid (171 mg, 0.892 mmol) was added followed by a 1:1 mixture of t-butanol and water (3 mL). Potassium osmate oxide hydrate (0.3 mg) was added followed by 4-methyl morpholine N-oxide (in 1.5 mL of water) and the reaction was allowed to stir overnight. The reaction was filtered and washed with water and 1 M hydrochloric acid to yield the title compound as a beige solid (95 mg, 68%).

$^1$H NMR (300 MHz, CD$_3$OD) δ 8.09 (s, 1H), 8.012 (dt, 1H), 7.58 (m, 2H), 7.25 (m, 5H), 5.15 (s, 2H).

Example 13.2

Synthesis of (2-m-Tolyl-2H-tetrazol-5-yl)-methanol

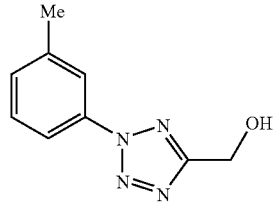

a) Synthesis of (m-Tolyl-hydrazono)-acetic acid

3-Methylphenylhydrazine hydrochloride (15.9 g, 100 mmol) was dissolved in water (450 mL) and ethanol (600 mL) with heating at 60° C. A solution of glyoxylic acid (9.21 g, 100 mmol) in water (100 mL) was added to the warm solution using water (3×15 mL) to rinse. The reaction mixture was stirred at 60° C. for 45 minutes and then cooled slightly and concentrated to remove ethanol. The aqueous mixture was neutralized with NaOH and then water was added (800 mL). The precipitate was filtered, washed with water (3×100 mL), washed with hexanes (100 mL) and dried to give the subtitle compound as a brown solid (12.2 g, 69%).

b) Synthesis of Azido-2,4,6-tribromobenzene 2,4,6-Tribromoaniline (34.16 g, 103.6 mmol) was mixed with acetic acid (600 mL) and sulfuric acid (130 mL) at room temperature. The mixture was stirred to obtain a solution and then cooled in an ice bath to an internal temperature of 10° C. A solution of NaNO$_2$ (7.65 g, 111 mmol) in water (22 mL) was added dropwise over 30 minutes while maintaining the internal temperature of the reaction mixture below 12° C. The reaction mixture was allowed to stir for 30 minutes at the same temperature. A solution of urea (0.90 g) in water (2 mL) was added and the mixture stirred for an additional 10 minutes. A solution of NaN$_3$ (7.65 g, 118 mmol) in water (22 mL) was slowly added and the mixture stirred for an additional 1 hour. Cold water (900 mL) was then slowly added in portions and the mixture stirred for 30 minutes. The precipitate was filtered, washed with water, dissolved in diethyl ether, dried over sodium sulfate and concentrated to give the subtitle compound as an off-white solid (34.2 g, 93%).

c) Synthesis of 2-m-Tolyl-2H-tetrazole-5-carboxylic acid ethyl ester

Ethanol (270 mL) was added to subtitle compound 13.2 a) (12.18 g, 68.3 mmol) followed by NaOEt (3.95 g, 206 mmol) and the subtitle compound 13.2 b) (26.8 g, 75.18 mmol). The resulting suspension was heated at 60° C. for 5 hours. The reaction mixture was poured into water (800 mL) while hot and the precipitate was filtered and washed with water. The filtrate was stirred with charcoal, filtered and then acidified to pH 1 using concentrated HCl. The precipitate was filtered, dissolved in ethyl acetate and the aqueous layer separated. The organic layer was washed once with water, dried over sodium sulfate and concentrated to give the product as an red solid. The solid obtained was mixed with pre-treated ethanol (200 mL with 38 mL of acetyl chloride at 0° C.) and the reaction mixture was heated at 85° C. for 24 hours and then concentrated. The residue was dissolved in dichloromethane and washed with water, aqueous saturated sodium bicarbonate and brine. The organic layer was concentrated and the residue was purified by silica gel using hexanes:ethyl acetate (95:5) to give the subtitle compound as a red oil (9.4 g, 59% over two steps).

$^1$H NMR (300 MHz, CDCl$_3$) δ 8.04 (s, 1H), 8.02 (d, 1H), 7.51 (t, 1H), 7.36 (d, 1H), 4.59 (q, 2H), 2.49 (s, 3H), 1.51 (t, 3H).

d) Synthesis of (2-m-Tolyl-2H-tetrazol-5-yl)-methanol

The subtitle compound 13.2 c) (9.42 g, 40.6 mmol) was mixed with methanol (95 mL) and the reaction mixture was heated to 60° C. Sodium borohydride (3.22 g, 85.2 mmol) was added carefully in small portions. The reaction mixture was stirred at 60° C. for 30 minutes and then concentrated. 1 M HCl (100 mL) was added and the mixture was then extracted twice with dichloromethane. The combined organic layer was washed with brine, dried over sodium sulfate and concentrated. The residue was purified by silica gel using 30% ethyl acetate:hexanes to give the title compound as a yellowish white solid (6.42 g, 83%).

$^1$H NMR (300 MHz, CDCl$_3$) δ 7.94 (s, 1H), 7.90 (d, 1H), 7.43 (t, 1H), 7.30 (d, 1H), 5.07 (d, 2H), 2.95 (t, 1H, OH), 2.47 (s, 3H).

Example 14.1

2-(3-Chloro-phenyl)-2H-tetrazole-5-carbaldehyde

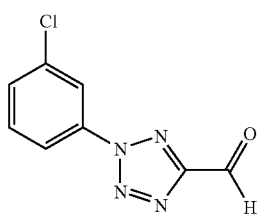

The crude product of the title compound from Example 13.1 (50.0 mg, 0.158 mmol) was weighed into a vial and toluene (3 mL) was added. Potassium carbonate (47.0 mg, 0.340 mmol) and lead (IV) acetate (70.0 mg, 0.158 mmol) were added with stirring. The reaction was allowed to stir for 2.5 hours. The reaction was filtered and ethyl acetate was added to the filtrate and an aqueous workup was done. The organic layer was washed with brine, dried over sodium sulfate, filtered and concentrated. The crude product was purified by column chromatography (40% EtOAc/hexanes) to yield the pure product as a white solid (22.3 mg, 68%).

$^1$H NMR (300 MHz, CDCl$_3$) δ 10.34 (s, 1H), 8.27 (s, 1H), 8.14 (m, 1H), 7.58 (d, 2H).

Example 14.2

2-(3-Chloro-phenyl)-2H-tetrazole-5-carbaldehyde

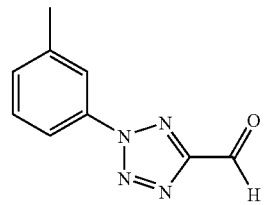

A solution of oxalyl chloride (4.0 mL, 46 mmol) in CH$_2$Cl$_2$ (100 mL) at −78° C. was added DMSO (6.5 mL, 92 mmol) dropwise. The mixture was stirred for 10 minutes after which the title compound from Example 13.2 (7.92 mg, 41.6 mmol) in CH$_2$Cl$_2$ (30 mL) was added dropwise. The mixture was stirred for an additional 30 minutes and Et$_3$N (2.9 mL, 208 mmol) was added dropwise. The reaction was then allowed to warm to room temperature. Water (150 mL) was then added and the organic layer was washed with brine, dried over sodium sulfate, filtered and concentrated. The crude product was purified by column chromatography (10-20% EtOAc/hexanes) to yield the title compound as an orange oil (4.98 g, 64%).

$^1$H NMR (300 MHz, CDCl$_3$) δ 10.33 (s, 1H), 8.04 (d, 1H), 8.00 (d, 1H), 7.49 (t, 1H), 7.39 (d, 1H), 2.50 (s, 3H).

The example below was prepared according to the above procedure for preparation of example 11.1 from example 14.1:

| Example | Structure | Name | Yield |
|---|---|---|---|
| 15.1 | 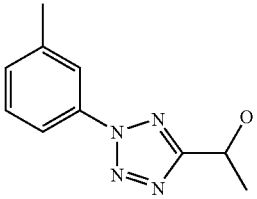 | 1-(2-m-Tolyl-2H-tetrazol-5-yl)-ethanol | 74% 4.02 g Yellow oil |
| $^1$H NMR | (300 MHz, CDCl$_3$) δ 7.90 (s, 1 H), 7.88 (d, 1 H), 7.39 (t, 1 H), 7.27 (d, 1 H), 5.32 (dq, 1 H), 2.97 (d, 1 H, OH), 2.46 (s, 3 H), 1.77 (d, 3 H) | | |

Example 16.1

(1R)-1-[5-(3-Chlorophenyl)isoxazol-3-yl]ethyl acetate

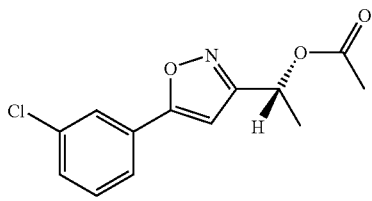

The title compound of Example 7.1 (106.5 g, 476 mmol) and Novozyme 435® (13 g) are taken up under Ar in dry toluene (1.5 L). After addition of vinyl acetate (66 mL, 716 mmol) the reaction was run at RT over night, followed by filtration over diatomaceous earth and washing with DCM. The solvent was evaporated in vacuo and the crude product was subjected to column chromatography on silica using dichloromethane/methanol (20:1) to give the title compound (50 g, 47%).

$^1$H NMR (300 MHz, CDCl$_3$) 7.76 (m, 1H), 7.65 (m, 1H), 7.41 (m, 2H), 6.54 (s, 1H), 6.07 (q, 1H), 2.13 (s, 3H), 1.66 (d, 3H). LC-MS (M$^+$+1)=266.

The following compounds were prepared in a similar manner:

| Example | Structure | Name | Yield |
|---|---|---|---|
| 16.2 | 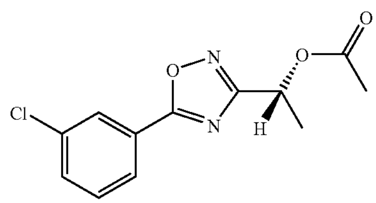 | (1R)-1-[5-(3-Chlorophenyl)-1,2,4-oxadiazol-3-yl]ethyl acetate | 7.1 g 49% |
| $^1$H NMR | (300 MHz, CDCl$_3$) δ 8.13 (t, 1 H), 8.01 (d, 1 H), 7.55 (d, 1 H), 7.47 (t, 1 H), 6.07 (q, 1 H), 2.15 (s, 3 H), 1.69 (d, 3 H). | | |
| 16.3 | 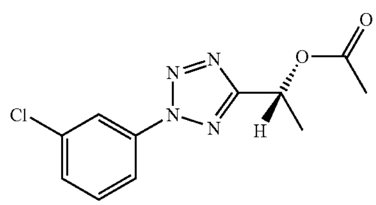 | (1R)-1-[2-(3-Chlorophenyl)-2H-tetrazol-5-yl]ethyl acetate | 1.13 g 58% |
| $^1$H NMR | (300 MHz, CDCl$_3$) δ 8.17 (s, 1 H), 8.06 (m, 1 H), 7.49 (m, 2 H), 6.29 (q, 1 H), 2.17 (s, 3 H), 1.79 (d, 3 H). | | |
| 16.4 | 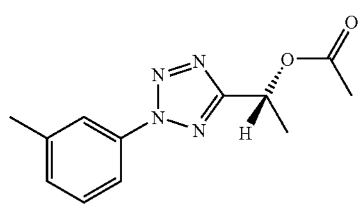 | (1R)-1-[2-(3-Methylphenyl)-2H-tetrazol-5-yl]ethyl acetate | 2.14 g |
| $^1$H NMR | (300 MHz, CDCl$_3$) δ 7.93 (s, 1 H), 7.90 (d, 1 H), 7.43 (t, 1 H), 7.28 (d, 1 H), 6.29 (q, 1 H), 2.48 (s, 3 H), 2.16 (s, 3 H), 1.76 (d, 3 H). | | |
| 16.5 | 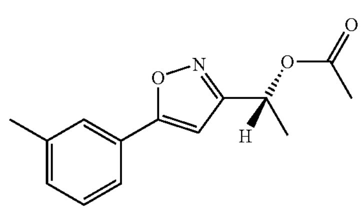 | (1R)-1-[5-(3-Methylphenyl)isoxazol-3-yl]ethyl acetate | 0.464 g |
| $^1$H NMR | (300 MHz, CDCl$_3$) δ 7.60 (s, 1 H), 7.58 (d, 1 H), 7.35 (t, 1 H), 7.27 (d, 1 H), 6.51 (s, 1 H), 6.07 (q, 1 H), 2.44 (s, 3 H), 2.10 (s, 3 H), 1.67 (d, 3 H). | | |

Example 17.1

(1R)-1-[5-(3-chlorophenyl)isoxazol-3-yl]ethanol

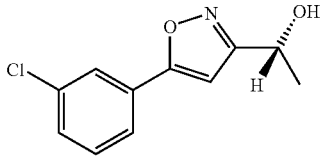

The title compound of Example 16.1 (56 g, 211 mmol) and lithium hydroxide monohydrate (10.6 g, 253 mmol) were mixed with THF/Water (7/5, 1.2 L) and stirred at RT over night. Reducing the volume of the mixture in vacuo to about half, followed by dilution with brine, extraction with ether and then drying over $MgSO_4$ and in vacuo concentration gave crude product. The crude product was purified by flash column chromatography on silica using heptane/EtOAc (7:3) to give the title compound (40 g, 85%).

$^1$H NMR (300 MHz, $CDCl_3$) 7.73 (m, 1H), 7.63 (m, 1H), 7.38 (m, 2H), 6.57 (s, 1H), 5.07 (q, 1H), 2.44 (s, 1H), 1.59 (d, 3H).

The following compounds were prepared in a similar manner:

| Example | Structure | Name | Yield |
|---|---|---|---|
| 17.2 | 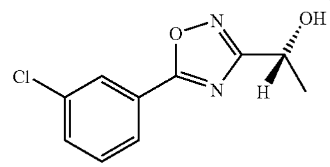 | (1R)-1-[5-(3-chlorophenyl)-1,2,4-oxadiazol-3-yl]ethanol | 5.8 g 97% |
| $^1$H NMR | (300 MHz, $CDCl_3$) δ 8.14 (s, 1 H), 8.02 (d, 1 H), 7.57 (d, 1 H), 7.47 (t, 1 H), 5.14-5.04 (m, 1 H), 2.42 (br, s, 1 H), 1.67 (d, 3 H) | | |
| 17.3 | 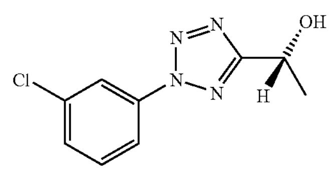 | (1R)-1-[2-(3-chlorophenyl)-2H-tetrazol-5-yl]ethanol | 0.95 g 99% |
| $^1$H NMR | (300 MHz, $CDCl_3$) δ 8.17 (s, 1 H), 8.06 (m, 1 H), 7.48 (m, 2 H), 5.31 (quint, 1 H), 2.51 (d, 1 H), 1.77 (d, 3 H) | | |
| 17.4 | 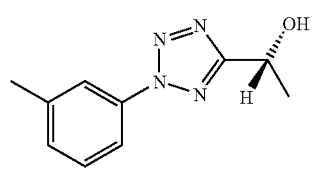 | (1R)-1-[2-(3-methylphenyl)-2H-tetrazol-5-yl]ethanol | 1.74 g |
| $^1$H NMR | (300 MHz, $CDCl_3$) δ 7.90 (s, 1 H), 7.88 (d, 1 H), 7.39 (t, 1 H), 7.27 (d, 1 H), 5.32 (dq, 1 H), 3.77 (d, 1 H, OH), 2.44 (s, 3 H), 1.76 (d, 3 H) | | |
| 17.5 | 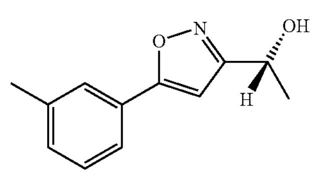 | (1R)-1-[5-(3-methylphenyl)-isoxazol-3-yl]ethanol | 0.356 g |
| $^1$H NMR | (300 MHz, $CDCl_3$) δ 7.60 (s, 1 H), 7.58 (d, 1 H), 7.35 (t, 1 H), 7.27 (d, 1 H), 6.56 (s, 1 H), 5.10 (dq, 1 H), 2.43 (s, 3 H), 2.28 (d, 1 H, OH), 1.60 (d, 3 H) | | |

Example 18.1

2-Oxo-1,2-dihydro-pyridine-4-carboxylic acid ethyl ester

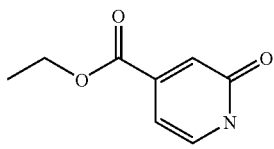

Acetyl chloride (20 mL) was added slowly to ethanol (80 mL) at room temperature. The clear solution was stirred for 5 minutes and then 2-hydroxy-4-pyridinecarboxylic acid (5.0 g, 35.9 mmol) was added as a solid. The reaction mixture was heated at reflux overnight. The reaction mixture was cooled to room temperature and the majority of the ethanol was evaporated. The residue was diluted with chloroform and water and the aqueous layer was neutralized by the careful addition of $K_2CO_3$. The organic layer was separated and the aqueous layer was extracted further with chloroform. The combined organic layer was dried over sodium sulfate and concentrated to give the title compound (5.74 g, 96%).

$^1$H NMR (300 MHz, $CDCl_3$) δ 7.48 (d, 1H), 7.23 (s, 1H), 6.82 (d, 1H), 4.39 (q, 2H), 1.4 (t, 3H).

Example 18.2

5-Methyl-2H-pyridazin-3-one

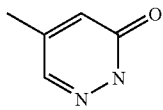

5-Hydroxy-4-methyl-5H-furan-2-one (10.0 g, 87.6 mmol) and hydrazine hydrate (4.38 g, 87.6 mmol) were stirred vigorously at r.t. for 1.5 hours in tetrahydrofuran. A solid began to precipitate and the reaction was heated at 60° C. overnight. The crude reaction mixture was concentrated onto silica gel and purified by column chromatography (0 to 10% methanol in 1:1 EtOAc/dichloromethane) to give 7.7 g (80%) of the title compound.

$^1$H NMR (300 MHz, $CDCl_3$) δ 11.38 (br, 1H), 7.66 (s, 1H), 6.74 (s, 1H), 2.25 (s, 3H).

Example 18.3

6-Oxo-1,6-dihydro-pyridazine-4-carboxylic acid

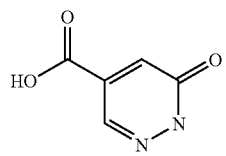

The title compound from Example 18.2 (0.90 g, 8.17 mmol) was stirred in concentrated sulfuric acid (13 mL) and heated to 45° C. Potassium permanganate (3.6 g, 12.25 mmol) was added portion wise over 30 min to avoid letting the temperature rise. The reaction was allowed to stir for a further 30 min at 45° C. The reaction was then cooled to r.t. and ice was added to the reaction mixture. The resulting precipitate was collected by vacuum filtration, washing with cold water and diethyl ether to give 0.978 g (87%) of the title compound as the a pale green solid.

$^1$H NMR (300 MHz, $CDCl_3$) δ 13.39 (br, 1H), 8.12 (s, 1H), 7.22 (s, 1H).

Example 18.4

6-Oxo-1,6-dihydro-pyridazine-4-carboxylic acid ethyl ester

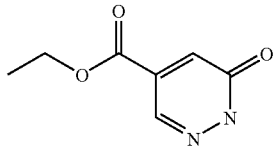

The title compound from Example 18.3 (1.0 g, 7.13 mmol) was added to a solution of ethanol (16 mL) and acetyl chloride (4 mL) and the resulting suspension was heated to 75° C. and stirred overnight. The reaction mixture was concentrated, diluted with water and extracted with dichloromethane. The organic phase was dried over sodium sulfate, filtered and concentrated to give the title compound.

$^1$H NMR (300 MHz, $CDCl_3$) δ 10.91 (br, 1H), 8.26 (s, 1H), 7.53 (s, 1H), 4.43 (q, 2H), 1.40 (t, 3H).

Example 19.1

2-Oxo-1-(2-trimethylsilanyl-ethoxymethyl)-1,2-dihydro-pyridine-4-carboxylic acid ethyl ester

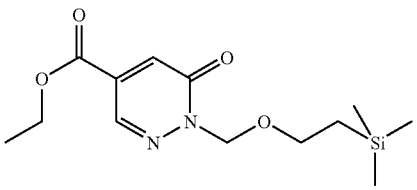

The title compound of example 18.1 (32 g, 191 mmol) and potassium carbonate (132 g, 957 mmol) were stirred in dimethylformamide (350 mL) at room temperature. Diisopropylethylamine (10 mL, 57 mmol) was added via a syringe, followed by 2-(trimethylsilyl)ethoxymethyl chloride (44.0 mL, 249 mmol). The reaction was stirred at room temperature and diisopropylethylamine (56.6 mL, 325 mmol) was added over 5 hours via a pressure equalized addition funnel. The reaction was then stirred overnight at room temperature. When TLC analysis showed that the reaction was complete the reaction mixture was diluted with ethyl acetate and washed four times with water and once with brine. The organic phase was dried over magnesium sulfate, filtered and concentrated. The residue was chromatographed on silica gel in 5-40% ethyl acetate in hexanes to purify the desired product (80%, trace amount of o-alkylated product observed).

¹H NMR (300 MHz, CDCl₃) δ 7.48 (d, 1H), 7.2 (d, 1H), 6.7 (dd, 1H), 5.36 (s, 2H), 4.37 (q, 2H), 3.61 (t, 2H), 1.38 (t, 3H), 0.96 (t, 2H), 0.00 (s, 9H).

Example 19.2

6-Oxo-1-(2-trimethylsilanyl-ethoxymethyl)-1,6-dihydro-pyridazine-4-carboxylic acid ethyl ester

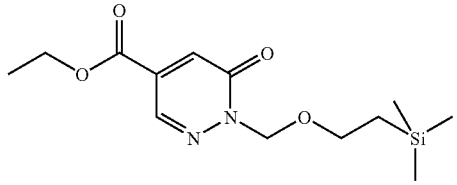

The title compound from Example 18.4 (0.90 g, 5.35 mmol) was stirred in dimethylformamide (20 mL) and diisopropyl ethylamine (1.39 mL, 8.025 mmol) at 0° C. and (2-chloromethoxy-ethyl)-trimethyl-silane (1.88 mL, 10.70 mmol) was added and the reaction was allowed to continue to stir at 0° C. for 2 hours and then overnight at r.t. The reaction mixture was diluted with EtOAc and washed with water and brine. The organic phase was dried over sodium sulfate, filtered and concentrated onto silica gel. The product was purified by column chromatography (0-20% EtOAc/hexanes) to afford the title compound as a clear oil (0.85 g, 53%).

¹H NMR (300 MHz, CDCl₃) δ 8.23 (d, 1H), 7.51 (s, 1H), 5.50 (s, 2H), 4.41 (q, 2H), 3.71 (m, 2H), 1.41 (t, 3H), 0.97 (m, 2H), 0.00 (s, 9H).

Example 20.1

2-Oxo-1-(2-trimethylsilanyl-ethoxymethyl)-1,2-dihydro-pyridine-4-carboxylic acid hydrazide

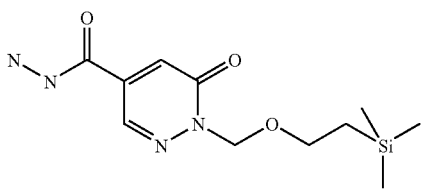

The title compound of example 19.1 (9.5 g, 32 mmol) was stirred in ethanol (100 mL) at 78° C. Hydrazine hydrate (7.8 mL, 159.7 mmol) was added and the reaction mixture was stirred at 78° C. for 3 hours. The reaction mixture was cooled to room temperature and concentrated to dryness. The residue was stirred in diethyl ether and filtered to give a yellow solid (8.5 g, 94%).

¹H NMR (300 MHz, CDCl₃) δ 8.5 (bs, 1H), 7.52 (d, 10H), 6.89 (d, 1H), 6.63 (dd, 1H), 5.36 (s, 2H), 3.62 (t, 2H), 2.9 (bs, 2H), 0.95 (t, 2H), 0.00 (s, 9H).

Example 20.2

6-Oxo-1-(2-trimethylsilanyl-ethoxymethyl)-1,6-dihydro-pyridazine-4-carboxylic acid hydrazide

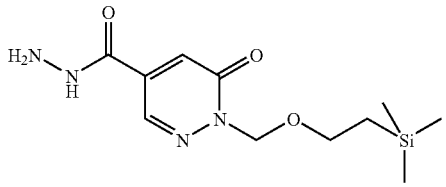

The title compound from Example 19.2 (0.85 g, 2.8 mmol) was stirred in ethanol. Hydrazine hydrate (0.720 g, 14.2 mmol) was added to the solution and the reaction was stirred at 50° C. for 1 hour. The reaction was concentrated and triturated with methanol and diethyl ether to produce a precipitate which was collected by vacuum filtration as the title compound (0.56 g, 57%).

¹H NMR (300 MHz, DMSO) δ 10.18 (br, 1H), 8.16 (d, 1H), 7.22 (d, 1H), 5.33 (s, 2H), 4.68 (s, 2H), 3.62 (t, 2H), 0.85 (t, 2H), −0.05 (s, 9H).

Example 21.1

4-(5-mercapto-4-methyl-4H-1,2,4-triazol-3-yl)-1-{[2-(trimethylsilyl)ethoxy]methyl}pyridin-2(1H)-one

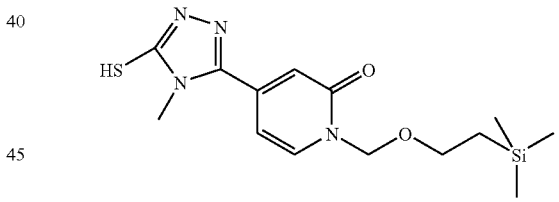

The title compound of Example 20.1 (19.0 g, 67.0 mmol) was stirred in methanol (150 mL) and heated to 60° C. Methyl isothiocyanate (5.04 mL, 73.7 mmol) was then added via a syringe. After stirring for 40 minutes, a solution on NaOH (2.95 g, 73.7 mmol) in water (30 mL) was added and the reaction mixture was stirred at 60° C. overnight. The reaction mixture was cooled to room temperature and concentrated. The aqueous residue was neutralized, extracted with chloroform, and the organic layer dried over sodium sulfate and concentrated. The residue was purified by silica gel using ethyl acetate to give the product (24.0 g, 56%).

¹H NMR (300 MHz, CDCl₃) δ 7.6 (d, 1H), 7.01 (d, 1H), 6.61 (dd, 1H), 5.42 (s, 2H), 3.74 (s, 3H), 3.66 (t, 2H), 0.96 (t, 2H), 0.00 (s, 9H).

In a similar manner the following compound was synthesized:

| Example | Structure | Name | Yield |
|---|---|---|---|
| 21.2 | 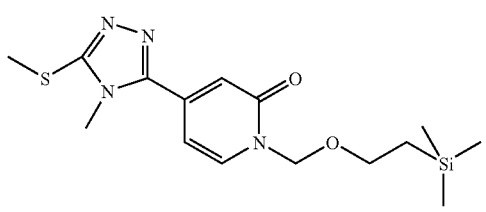 | 5-(5-Mercapto-4-methyl-4H-[1,2,4]triazol-3-yl)-2-(2-trimethylsilanyl-ethoxymethyl)-2H-pyridazin-3-one | 86% 3.14 g |
| $^1$H NMR | (300 MHz, CDCl$_3$) δ 11.86 (br, 1 H), 8.22 (d, 1 H), 7.31 (d, 1 H), 5.53 (s, 2 H), 3.76 (m, 5 H), 1.00 (m, 2 H), 0.01 (s, 9 H) | | |

Example 22.1

4-[4-methyl-5-(methylthio)-4H-1,2,4-triazol-3-yl]-1-{[2-(trimethylsilyl)ethoxy]methyl}pyridin-2(1H)-one

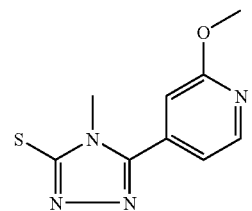

The title compound of example 21.1 (21.6 g, 63.8 mmol) was dissolved in a solution of NaOH (5.36 g, 134 mmol) in water (134 mL). When a clear solution was observed, ethanol (40 mL) was added followed by iodomethane (6.37 mL, 102 mmol). The reaction mixture was stirred overnight at room temperature. The reaction mixture was then extracted four times with chloroform and the combined organic layer was dried over sodium sulfate and concentrated to give the title product (22.0 g, 98%).

$^1$H NMR (300 MHz, CDCl$_3$) δ 7.53 (d, 1H), 6.74 (m, 2H), 5.36 (s, 2H), 3.67 (s, 3H), 3.63 (t, 2H), 2.77 (s, 3H), 0.95 (t, 2H), 0.00 (s, 9H).

Example 23.1

2-Methoxy-isonicotinic acid hydrazide

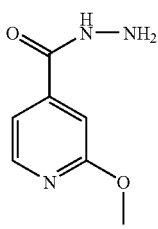

2-Methoxy-isonicotinic acid methyl ester (23.0 g, 137 mmol) and hydrazine hydrate (8.95 g, 178 mmol) were dissolved in ethanol and stirred at 75° C. for 12 hours. The reaction mixture was concentrated and the remaining solid was tritiated in hexanes/ether (80:20), filtered and dried to afford the title compound as a solid (18.4 g, 80%).

$^1$H NMR (300 MHz, CDCl$_3$) δ 8.28 (d, 1H), 7.54 (bs, 1H), 7.15 (dd, 1H), 7.05 (s, 1H), 3.99 (s, 3H).

Example 24.1

5-(2-Methoxy-pyridin-4-yl)-4-methyl-4H-[1,2,4]triazole-3-thiol

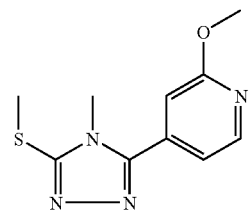

The title compound of example 23.1 (18.35 g, 109.8 mmol) and methyl isothiocyanate (8.83 g, 120 mmol) were stirred together at 60° C. for 30 minutes. Sodium hydroxide (4.83 g, 120 mmol) in water (32 mL) was added to the reaction mixture it was allowed to continue to stir at 60° C. for 12 hours. The reaction mixture was concentrated and diluted with water. It was acidified to pH 4-5 with 3 M HCl. A solid precipitated out which was filtered, washing with portions of water, then dried to afford the product as a beige solid (21.2 g, 87%).

$^1$H NMR (300 MHz, CDCl$_3$) δ 8.37 (dd, 1H), 7.12 (dd, 1H), 6.99 (s, 1H), 4.01 (s, 3H), 3.71 (s, 3H).

Example 25.1

2-Methoxy-4-(4-methyl-5-methylsulfanyl-4H-[1,2,4]triazol-3-yl)-pyridine

The title compound of example 24.1 (21.30 g, 95.83 mmol) was set stirring in 1 M sodium hydroxide in a cold water bath. Iodomethane (21.76 g, 153.3 mmol) in ethanol (63 mL) was added to the reaction. As the reaction progressed, solid began to precipitate out. The reaction was allowed to stir at RT for 12 hours. The reaction mixture was extracted with dichloromethane and the organic extracts were washed with brine, dried and concentrated to afford the title compound as a white solid (22 g, 97%).

$^1$H NMR (300 MHz, CDCl$_3$) δ 8.32 (dd, 1H), 7.20 (dd, 1H), 7.01 (s, 1H), 3.99 (s, 3H), 3.64 (s, 3H), 2.80 (s, 3H).

In a similar manner the following compound was synthesized:

| Example | Structure | Name | Yield |
|---|---|---|---|
| 25.2 | 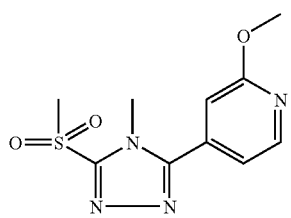 | 5-(4-Methyl-5-methylsulfanyl-4H-[1,2,4]triazol-3-yl)-2-(2-trimethylsilanyl-ethoxymethyl)-2H-pyridazin-3-one | 91% 1.15 g |

$^1$H NMR (300 MHz, CDCl$_3$) δ 8.43 (d, 1 H), 7.09 (d, 1 H), 5.49 (s, 2 H), 3.74 (m, 5 H), 2.82 (s, 3 H), 0.98 (m, 2 H), 0.01 (s, 9 H)

Example 26.1

4-(5-Methanesulfonyl-4-methyl-4H-[1,2,4]triazol-3-yl)-2-methoxy-pyridine

The title compound of example 25.1 (21.97 g, 92.97 mmol) was partially dissolved in methanol (500 mL) and OXONE® (potassium peroxomonosulfate compound, 114.3 g, 186.0 mmol) dissolved in water (500 mL) was added slowly. The reaction mixture stirred for 5 hours. The reaction was partially concentrated, poured into water and extracted with chloroform. The organic extracts were dried, filtered and concentrated to afford the title compound (22 g, 93%) as a white solid.

$^1$H NMR (300 MHz, CDCl$_3$) δ 8.38 (dd, 1H), 7.17 (dd, 1H), 7.02 (s, 1H), 4.04 (s, 3H), 4.02 (s, 3H), 3.61 (s, 3H).

Example 27.1

4-(5-Methanesulfonyl-4-methyl-4H-[1,2,4]triazol-3-yl)-1H-pyridin-2-one

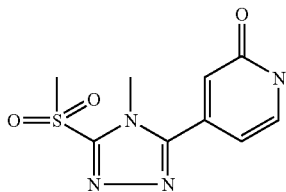

The title compound of example 26.1 (6.4 g, 23.9 mmol) was dissolved in acetic acid (190 mL) and 20-30% hydrogen bromide in ethanol (190 mL) was added to the reaction. It was allowed to stir at 80° C. for 3.5 hours. The reaction was concentrated once, diluted with ethanol and concentrated again. Ethanol was added once more and the mixture was sonicated until a precipitate formed. The solid was filtered and dried under vacuum to afford the title compound (6.77 g, 85%) as a white solid.

$^1$H NMR (300 MHz, CDCl$_3$) δ 3.59 (s, 3H); 3.90 (s, 3H); 6.45 (d, 1H); 6.71 (s, 1H); 7.59 (d, 1H).

Example 28.1

4-(5-Methanesulfonyl-4-methyl-4H-[1,2,4]triazol-3-yl)-1-(2-trimethylsilanyl-ethoxymethyl)-1H-pyridin-2-one

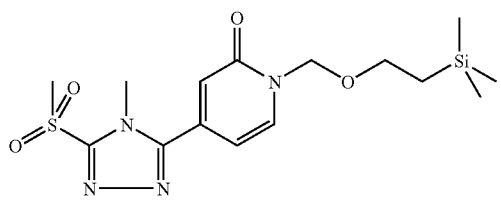

Procedure A

The title compound of example 27.1 was dissolved in dichloromethane at 0° C. and 4-(dimethylamino)pyridine (29 mg), N,N-diisopropylethylamine (8.8 mL, 50.5 mmol) and 2-(trimethylsilyl)ethoxymethyl chloride (7.9 mL, 44.4 mmol) were added. The reaction was allowed to stir at 0° C. for 1 hour and then warmed to r.t. for 2.5 hours. The reaction was diluted with dichloromethane, washed with portions of water, dried filtered and concentrated. The crude product was purified by column chromatography to afford the product (5.15 g, 66%) as a white foamy solid.

$^1$H NMR (300 MHz, CDCl$_3$) δ 7.62 (d, 1H), 6.79 (d, 1H), 6.65 (dd, 1H), 5.4 (s, 2H), 4.04 (s, 3H), 3.68 (t, 2H), 3.6 (s, 3H), 0.98 (t, 2H), 0.02 (s, 9H).

Procedure B

To a solution of the title compound of example 22.1 (22.0 g, 62.4 mmol) in methanol (250 mL) was added a solution of OXONE® (76.7 g, 125 mmol) in water (320 mL). White precipitate formed. The reaction mixture was stirred at room temperature for 4 hours. The reaction mixture was then diluted with water and extracted four times with chloroform. The organic layer was dried over sodium sulfate and concentrated. The residue was purified by silica gel using ethyl acetate:methanol (100:0 to 90:10) to give the title compound as a sticky white foam (21.0 g, 87%).

$^1$H NMR (300 MHz, CDCl$_3$) δ 7.62 (d, 1H), 6.79 (d, 1H), 6.65 (dd, 1H), 5.4 (s, 2H), 4.04 (s, 3H), 3.68 (t, 2H), 3.6 (s, 3H), 0.98 (t, 2H), 0.02 (s, 9H).

Example 28.2

5-(5-Methanesulfonyl-4-methyl-4H-[1,2,4]triazol-3-yl)-2-(2-trimethylsilanyl-ethoxymethyl)-2H-pyridazin-3-one

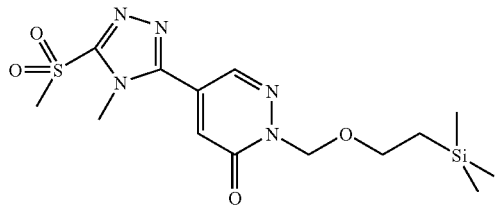

To the title compound from example 25.2 (0.22 g, 0.62 mmol) in methanol (2.3 mL) was added OXONE® (0.766 g, 1.25 mmol) in water (3.1 mL). The reaction was stirred for 5 hours at r.t. The reaction mixture was partitioned between dichloromethane and water and the aqueous layer was extracted with portions of dichloromethane. The organic extracts were dried over sodium sulfate, filtered and concentrated. The product was purified by column chromatography (100% EtOAc) to give the title compound (0.172 g, 72%) as a white solid.

$^1$H NMR (300 MHz, CDCl$_3$) δ 8.43 (s, 1H), 7.09 (s, 1H), 5.52 (s, 2H), 3.75 (m, 5H), 2.82 (s, 1H) 1.00 (m, 2H), 0.02 (s, 9H).

Example 29.1

2-Benzyloxy-4-(5-methanesulfonyl-4-methyl-4H-[1,2,4]triazol-3-yl)-pyridine

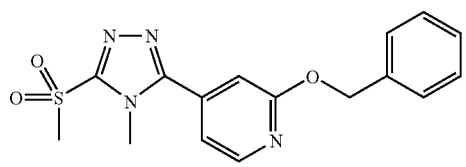

The title compound from example 27.1 (0.95 g, 3.7 mmol) and silver (1) carbonate (1.23 g, 4.48 mmol) were combined in a round bottom flask and purged with nitrogen. Toluene (10 mL) was added, followed by benzyl bromide (0.53 mL, 4.48 mmol) and the reaction was stirred for 72 h at room temperature. The silver salts were then removed by filtration through diatomaceous earth, which were then washed with dichloromethane. The filtrate was concentrated then purified by column chromatography on silica gel with 0-10% ethyl acetate in dichloromethane to give the title compound (off-white solid, 549 mg, 43

$^1$H NMR (300 MHz, CDCl$_3$) δ 3.52 (s, 3H); 3.93 (s, 3H); 5.44 (s, 3H); 7.06 (d, 1H); 7.17 (dd, 1H); 7.34 (m, 3H); 7.47 (m, 2H); 8.33 (d, 1H).

Example 30.1

1-Methyl-2-oxo-1,2-dihydro-pyridine-4-carboxylic acid methyl ester

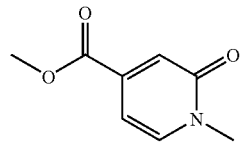

2-Oxo-1,2-dihydropyridine-4-carboxylic acid (5.0 g, 36 mmol) and potassium carbonate (24.8 g, 179 mmol) were stirred in DMF (75 mL) at room temperature. Iodomethane (6.72 mL, 108 mmol) was added slowly via a syringe and the reaction mixture was stirred for 3 days at room temperature. The reaction mixture was then diluted with water and extracted with dichloromethane until the product was removed from the aqueous phase. The combined organics were dried over magnesium sulfate, filtered and concentrated, then chromatographed in ethyl acetate on silica gel to yield the title compound (4 g, 66%).

$^1$H NMR (300 MHz, CDCl$_3$) δ 3.57 (s, 3H); 3.89 (s, 3H); 6.65 (d, 1H); 7.14 (s, 1H); 7.39 (d, 1H).

Example 31.1

1-Methyl-2-oxo-1,2-dihydro-pyridine-4-carboxylic acid hydrazide

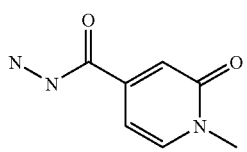

The title compound from example 30.1 (4 g, 24 mmol) was dissolved in ethanol and stirred at 78° C. Hydrazine hydrate (5.8 mL, 120 mmol) was added via a syringe and the reaction was stirred for 3 h at 78° C., at which time the starting material was no longer visible by TLC. The reaction mixture (clear solution) was then cooled to room temperature, and diluted

Example 32.1

4-(5-Mercapto-4-methyl-4H-[1,2,4]triazol-3-yl)-1-methyl-1H-pyridin-2-one

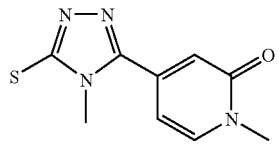

The title compound of example 31.1 (1.0 g, 5.98 mmol) was stirred in methanol (6 mL) at 60° C. Methyl isothiocyanate (481 mg, 6.58 mmol) was dissolved in methanol (2 mL) and added to the reaction mixture which was stirred for 15 min. After 15 min a solution of sodium hydroxide (263 mg) in water (2 mL) was added to the reaction mixture which was kept stirring at 60° C. overnight. The reaction mixture was then concentrated in vacuo to remove the methanol and the remaining residue was stirred in 3 M HCl (aq) to precipitate the product which was collected by vacuum filtration (off-white powder, 1.2 g, 90%).

$^1$H NMR (300 MHz, CDCl$_3$) δ: 3.47 (s, 3H); 3.57 (s, 3H); 6.51 (d, 1H); 6.78 (s, 1H); 7.86 (d, 1H); 14.09 (sb, 1H).

Example 33.1

1-Methyl-4-(4-methyl-5-methylsulfanyl-4H-[1,2,4]triazol-3-yl)-1H-pyridin-2-one

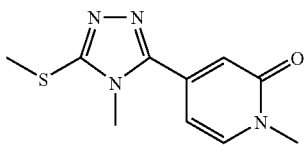

The title compound from example 32.1 (600 mg, 2.7 mmol) was dissolved in a solution of sodium hydroxide (216 mg, 5.4 mmol) and water (5 mL). When a clear, uniform solution was observed ethanol (6 mL) was added, followed by iodomethane (268 μL, 4.3 mmol). The reaction was stirred at room temperature for 6 h. The reaction mixture was then diluted with water and extracted four times with chloroform. The organic phase was dried over magnesium sulfate, filtered and concentrated to yield the title compound (yellowish solid, 500 mg, 78%).

$^1$H NMR (300 MHz, CDCl$_3$) δ 2.79 (s, 3H); 3.61 (s, 3H); 3.69 (s, 3H); 6.74 (m, 2H); 7.42 (d, 1H).

Example 34.1

4-(5-Methanesulfonyl-4-methyl-4H-[1,2,4]triazol-3-yl)-1-methyl-1H-pyridin-2-one

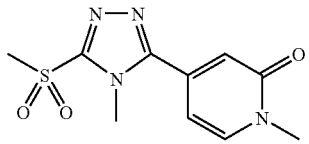

The title compound from example 33.1 (500 mg, 2.11 mmol) was dissolved in glacial acetic acid (6.5 mL). To this solution was added a solution of potassium permanganate (501 mg, 3.18 mmol). The resulting brown reaction mixture was stirred at room temperature for 3 h. When TLC analysis confirmed consumption of all starting material, the reaction was quenched by addition of sodium sulfite (saturated aqueous solution), then neutralized by careful addition of potassium carbonate solution. The product was extracted with three times with chloroform. The combined organics were dried over magnesium sulfate, filtered and concentrated, then chromatographed in 0-10% methanol in ethyl acetate on silica gel to give the final product (pale off-white solid, 327 mg, 57%).

$^1$H NMR (300 MHz, CDCl$_3$) δ 3.59 (s, 3H); 3.62 (s, 3H); 4.02 (s, 3H); 6.58 (dd, 1H); 6.79 (d, 1H); 7.48 (d, 1H).

Example 35.1

2-Benzyloxy-4-(5-{1-[5-(3-chloro-phenyl)-isoxazol-3-yl]-ethoxy}-4-methyl-4H-[1,2,4]triazol-3-yl)-pyridine

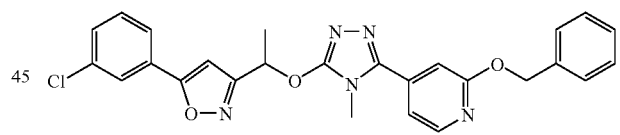

The title compound from example 29.1 (103 mg, 0.298 mmol), the title compound from example 7.1 (100 mg, 0.4471 mmol) and cesium carbonate (291 mg, 0.894 mmol) were combined in a screw cap vial which was purged with nitrogen. Dimethylformamide (3 mL) was added and the reaction was stirred at 65° C. overnight. The reaction mixture was then cooled to room temperature, diluted with water and extracted three times with dichloromethane. The combined organics were dried over magnesium sulfate, filtered and concentrated, then chromatographed in dichloromethane followed by ethyl acetate on silica gel to give the title compound (129.4 mg, 58%).

$^1$H NMR (300 MHz, CDCl$_3$) δ 1.91 (d, 3H); 3.56 (s, 3H); 5.41 (s, 2H); 6.33 (q, 1H); 6.72 (s, 1H); 7.04 (s, 1H); 7.25 (d, 1H); 7.35 (m, 5H); 7.46 (m 2H); 7.63 (m, 1H); 7.73 (s, 1H); 8.27 (d, 1H).

--- with diethyl ether to precipitate the product which was collected by vacuum filtration to yield the title compound as a pale yellow solid (3.13 g, 78%).

$^1$H NMR (300 MHz, CDCl$_3$) δ 3.42 (s, 3H); 4.53 (sb, 2H); 6.48 (d, 1H); 6.73 (s, 1H); 7.75 (d, 1H); 9.90 (sb, 1H).

The following compounds were synthesized in a similar fashion:

| Example | Structure | Name | Yield |
|---|---|---|---|
| 35.2 | 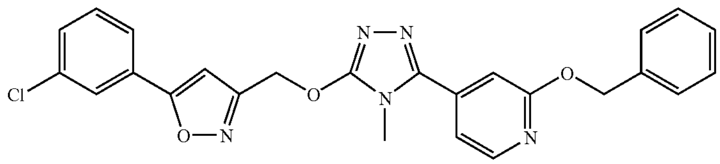 | 2-Benzyloxy-4-{5-[5-(3-chloro-phenyl)-isoxazol-3-ylmethoxy]-4-methyl-4H-[1,2,4]triazol-3-yl}-pyridine | 64.5 mg<br>78%<br>Clear oil |
| ¹H NMR | (300 MHz, CDCl₃) δ 3.63(s, 3H); 5.44(s, 2H); 5.69(s, 2H); 6.84(s, 1H); 7.07(s, 1H); 7.28(m, 1H); 7.40(m, 5H); 7.49(m, 2H); 7.69(m, 1H); 7.79(s, 1H); 8.32(d, 1H) | | |
| 35.3 | 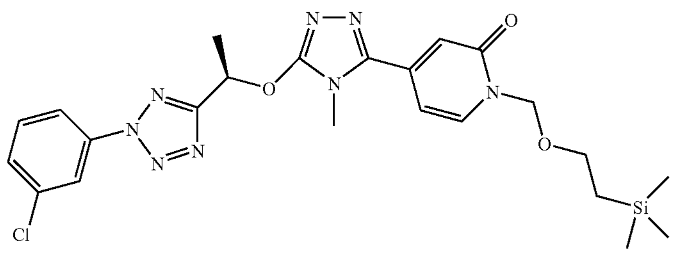 | 4-(5-{(1R)-1-[2-(3-chlorophenyl)-2H-tetrazol-5-yl]ethoxy}-4-methyl-4H-1,2,4-triazol-3-yl)-1-{[2-(trimethylsilyl)ethoxy]methyl}pyridin-2(1H)-one | 241 mg<br>66%<br>Yellow oil |
| ¹H NMR | (300 MHz, CDCl₃) δ 0.97(t, 2H); 2.03(d, 3H); 3.65(s, 3H); 3.65(t, 2H); 5.38(s, 2H); 6.59(q, 1H); 6.75(s, 1H); 6.83(d, 1H); 7.51(m, 3H); 8.06(m, 1H); 8.18(s, 1H) | | |
| 35.4 | 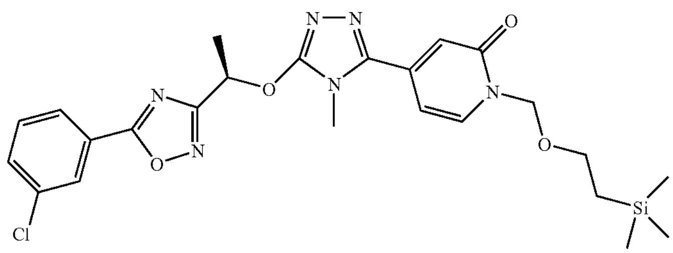 | 4-(5-{(1R)-1-[5-(3-chlorophenyl)-1,2,4-oxadiazol-3-yl]ethoxy}-4-methyl-4H-1,2,4-triazol-3-yl)-1-{[2-(trimethylsilyl)ethoxy]methyl}pyridin-2(1H)-one | 6.59 g<br>79%<br>White foamy solid |
| ¹H NMR | (300 MHz, CDCl₃) δ 8.15(t, 1H); 8.04(m, 1H); 7.58(m, 1H); 7.51(m, 2H); 6.84(dd, 1H); 6.75(d, 1H); 6.4(q, 1H); 5.38(s, 2H); 3.67(s, 3H); 3.65(t, 2H); 1.95(d, 3H); 0.97(t, 2H); 0.01(s, 9H) | | |
| 35.5 | 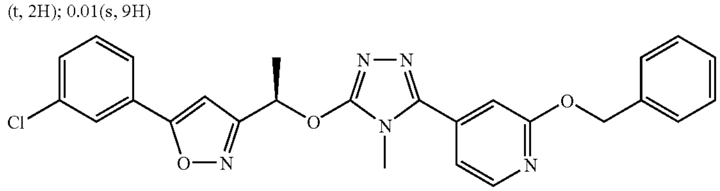 | 2-Benzyloxy-4-(5-{(R)-1-[5-(3-chloro-phenyl)-isoxazol-3-yl]-ethoxy}-4-methyl-4H-[1,2,4]triazol-3-yl)-pyridine | 200 mg<br>70%<br>Clear oil, |
| ¹H NMR | 1.91(d, 3H); 3.56(s, 3H); 5.41(s, 2H); 6.33(q, 1H); 6.72(s, 1H); 7.04(s, 1H); 7.25(d, 1H); 7.35(m, 5H); 7.46(m, 2H); 7.63(m, 1H); 7.73(s, 1H); 8.27(d, 1H) | | |
| 35.6 | 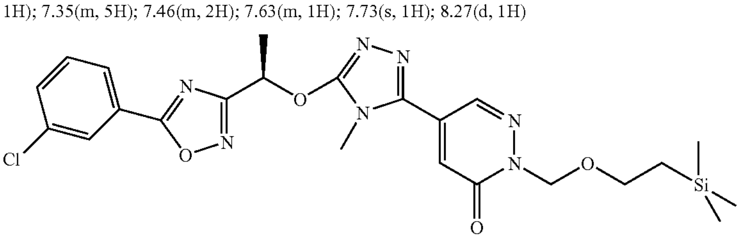 | 5-(5-{1-[5-(3-Chloro-phenyl)-[1,2,4]oxa-diazol-3-yl]-ethoxy}-4-methyl-4H-[1,2,4]triazol-3-yl)-2-(trimethylsilanyl-ethoxymethyl)-2H-pyridazin-3-one | 0.054 g<br>23% |
| ¹H NMR | (300 MHz, CDCl₃) δ 8.47(d, 1H); 8.13(s, 1H); 8.02(m, 1H); 7.59(m, 1H); 7.50(t, 1H); 7.07(d, 1H); 6.40(q, 1H); 5.50(s, 2H); 3.73(m, 5H); 1.96(d, 3H); 0.99(m, 2H) | | |

-continued

| Example | Structure | Name | Yield |
|---|---|---|---|
| 35.7 | 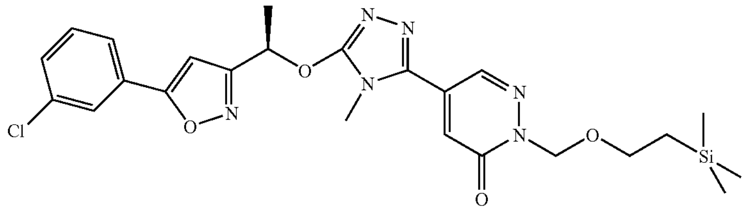 | 5-(5-{1-[5-(3-Chloro-phenyl)-isoxazol-3-yl]-ethoxy}-4-methyl-4H-[1,2,4]triazol-3-yl)-2-(2-trimethylsilanyl-ethoxymethyl)-2H-pyridazin-3-one | 0.145 g 43% |
| ¹H NMR | (300 MHz, CDCl₃) δ 8.46(s, 1H); 7.85(s, 1H); 7.74(m, 1H); 7.66(m, 2H); 7.05(d, 1H); 6.69(s, 1H); 6.34(q, 1H); 5.49(s, 2H); 3.72(t, 2H); 3.65(s, 3H); 1.92(d, 3H); 0.98(m, 2H); 0.00(s, 9H) | | |
| 35.8 | 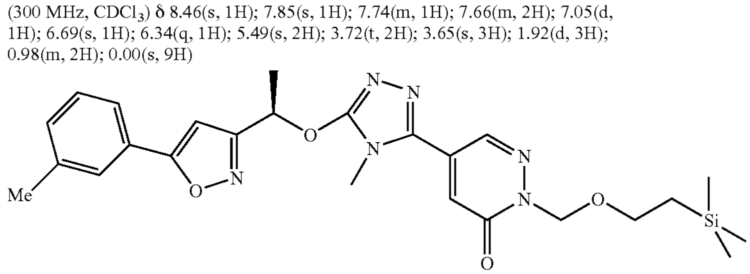 | 5-(5-{1-[5-(3-Methyl-phenyl)-isoxazol-3-yl]-ethoxy}-4-methyl-4H-[1,2,4]triazol-3-yl)-2-(2-trimethylsilanyl-ethoxymethyl)-2H-pyridazin-3-one | 0.120 g 45% |
| ¹H NMR | (300 MHz, CDCl₃) δ 8.49(s, 1H); 7.82(s, 1H); 7.79(m, 1H); 7.36(t, 1H); 7.26(d, 1H); 7.06(d, 1H); 6.64(s, 1H); 6.36(q, 1H); 5.58(s, 2H); 3.74(t, 2H); 3.66(s, 3H); 2.42(s, 3H); 1.93(d, 3H); 0.98(t, 2H); 0.00 (s, 9H) | | |
| 35.9 | 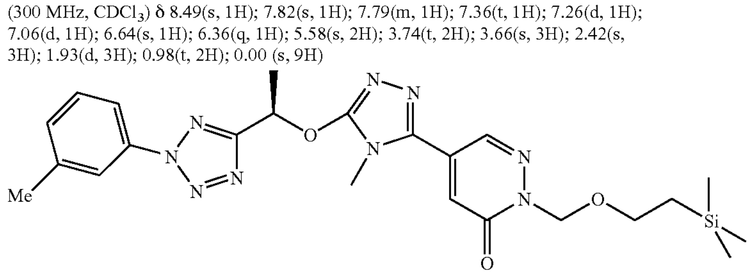 | 5-(5-{1-[2-(3-Methyl-phenyl)-2H-tetrazol-5-yl]-ethoxy}-4-methyl-4H-[1,2,4]triazol-3-yl)-2-(2-trimethylsilanyl-ethoxymethyl)-2H-pyridazin-3-one | 0.603 g 97%, |
| ¹H NMR | (300 MHz, CDCl₃) δ 8.48(d, 1H); 7.94(d, 1H); 7.91(d, 1H); 7.44(t, 1H); 7.31(d, 1H); 7.05(d, 1H); 6.60(q, 1H); 5.50(s, 2H); 3.73(t, 2H); 3.68(s, 3H); 2.48(s, 3H); 2.02(d, 3H); 0.99(t, 2H); 0.00(s, 9H) | | |
| 35.10 | 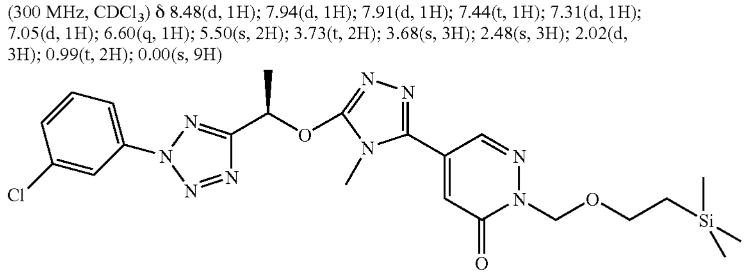 | 5-(5-{1-[2-(3-Chloro-phenyl)-2H-tetrazol-5-yl]-ethoxy}-4-methyl-4H-[1,2,4]triazol-3-yl)-2-(2-trimethylsilanyl-ethoxymethyl)-2H-pyridazin-3-one | 0.136 g 58%, |
| ¹H NMR | (300 MHz, CDCl₃) δ 8.46(d, 1H); 8.16(s, 1H); 8.05(m, 1H); 7.50(m, 2H); 7.06(d, 1H); 6.60(q, 1H); 5.52(s, 2H); 3.70(m, 5H); 2.03(d, 3H); 0.99(m, 2H); 0.00(s, 9H) | | |

Example 36.1

4-(5-{(1R)-1-[5-(3-Chlorophenyl)isoxazol-3-yl]ethoxy}-4-methyl-4H-1,2,4-triazol-3-yl)-1-methylpyridin-2(1H)-one

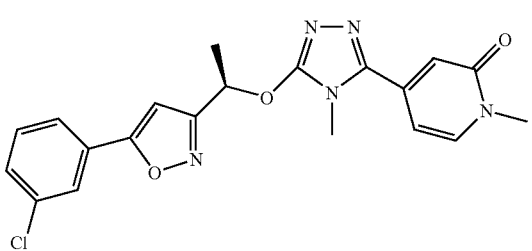

The title compound from example 17.1 (96 mg, 0.43 mmol), the title compound from example 34.1 (100 mg, 0.36 mmol) and cesium carbonate (419 mg, 1.29 mmol) were combined with a stir bar in a screw cap vial which was purged with nitrogen. The combined reagents were stirred in DMF and heated to 60° C. overnight. The reaction mixture was then diluted with water and extracted three times with chloroform. The organic phase was dried over magnesium sulfate, filtered and concentrated then chromatographed in 0-10% methanol in ethyl acetate (pale solid, 105 mg, 68%).

¹H NMR (300 MHz, CDCl₃) δ 1.89 (d. 3H); 3.56 (s, 3H); 3.57 (s, 3H); 6.31 (q, 1H); 6.73 (m, 3H); 7.38 (m, 3H); 7.64 (m, 1H); 7.73 (s, 1H).

The following compound(s) were made in a similar manner:

| Example | Structure | Name | Yield |
|---|---|---|---|
| 36.2 | 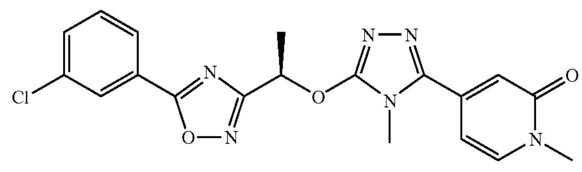 | 4-(5-{(R)-1-[5-(3-Chloro-phenyl)-[1,2,4]oxadiazol-3-yl]-ethoxy}-4-methyl-4H-[1,2,4]triazol-3-yl)-1-methyl-1H-pyridin-2-one | 40% |
| ¹H NMR | (300 MHz, CDCl₃) δ 1.93 (d, 3 H); 3.57 (s, 3 H); 3.63 (s, 3 H); 6.38 (q, 1 H); 6.76 (m, 2 H); 7.37 (d, 1 H); 7.47 (t, 1 H); 7.55 (m, 1 H); 8.00 (d, 1 H); 8.11 (s, 1 H) | | |
| 36.3 | 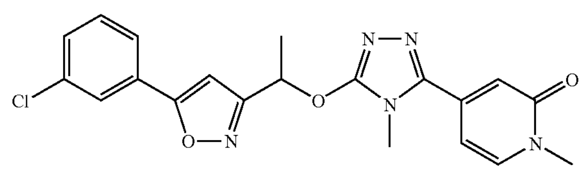 | 4-(5-{1-[5-(3-Chloro-phenyl)-isoxazol-3-yl]-ethoxy}-4-methyl-4H-[1,2,4]triazol-3-yl)-1-methyl-1H-pyridin-2-one | 57% |
| ¹H NMR | (300 MHz, CDCl₃) δ 1.89 (d. 3 H); 3.56 (s, 3 H); 3.57 (s, 3 H); 6.31 (q, 1 H); 6.73 (m, 3 H); 7.38 (m, 3 H); 7.64 (m, 1 H); 7.73 (s, 1 H) | | |
| 36.4 | 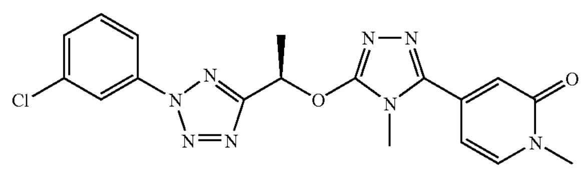 | 4-(5-{(R)-1-[2-(3-Chloro-phenyl)-2H-tetrazol-5-yl]-ethoxy}-4-methyl-4H-[1,2,4]triazol-3-yl)-1-methyl-1H-pyridin-2-one | 83% |
| ¹H NMR | (300 MHz, CDCl₃) δ 2.00 (d, 3 H); 3.57 (s, 3 H); 3.62 (s, 3 H); 6.56 (q, 1 H); 6.75 (m, 2 h); 7.38 (D, 1 h); 7.48 (M, 2 h); 8.03 (m, 1 H); 8.14 (s, 1 H) | | |

Example 37.1

4-(5-{1-[5-(3-Chloro-phenyl)-isoxazol-3-yl]-ethoxy}-4-methyl-4H-[1,2,4]triazol-3-yl)-1H-pyridin-2-one Procedure A

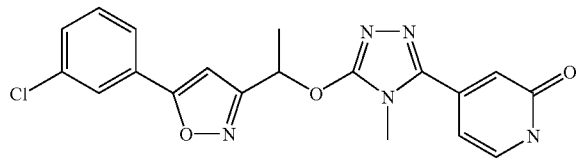

The title compound of example 35.1 (125 mg, 0.256 mmol) was stirred in ethanol (2 mL). Palladium on carbon (10%, 50 mg) was added and the reaction was stirred under hydrogen (balloon pressure) overnight. The reaction mixture was then diluted with dichloromethane and filtered to remove the palladium catalyst. The filtrate was concentrated, then chromatographed in 10% methanol in ethyl acetate to yield the desired product (38.5 mg, 38%).

¹H NMR (300 MHz, CDCl₃) δ 1.88 (d, 3H); 3.65 (s, 3H); 4.34 (sb, 1H); 6.26 (q, 1H); 6.73 (m, 3H); 7.42 (m, 3H); 7.66 (m, 1H); 7.75 (s, 1H).

The following compounds were synthesized in a similar fashion:

| Example | Structure | Name | Yield |
|---|---|---|---|
| 37.2 | 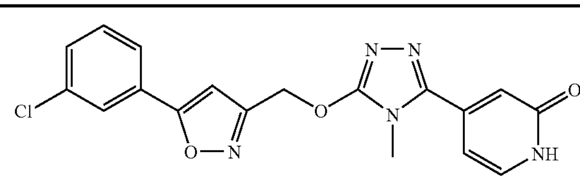 | 4-{5-[5-(3-Chloro-phenyl)-isoxazol-3-ylmethoxy]-4H-[1,2,4]triazol-3-yl}-1H-pyridin-2-one | 15.2 mg 30% Clear oil |
| ¹H NMR | (300 MHz, CDCl₃) δ 3.59 (s, 3 H); 3.97 (sb, 1 H); 5.62 (s, 2 H); 6.72 (m, 2 H); 6.80 (s, 1 H); 7.41 (m, 3 H); 7.69 (m, 1 H); 7.76 (s, 1 H) | | |

| Example | Structure | Name | Yield |
|---|---|---|---|
| 37.3 | 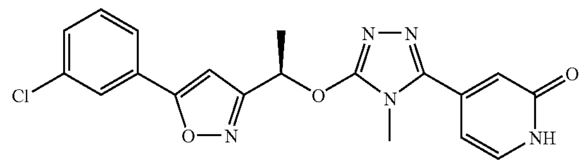 | 4-(5-{(R)-1-[5-(3-Chloro-phenyl)-isoxazol-3-yl]-ethoxy}-4H-[1,2,4]triazol-3-yl)-1H-pyridin-2-one | 165 mg<br>100%<br>White solid |

¹H NMR (300 MHz, CDCl₃) δ 1.92 (d, 3 H); 3.62 (s, 3 H); 6.34 (q, 1 H); 6.71 (s, 1 H); 6.78 (s, 1 H); 6.84 (d, 1 H); 7.40 (m, 2 H); 7.49 (d, 1 H); 7.65 (m, 1 H); 7.75 (s, 1 H)

Example 38.1

4-(5-{(R)-1-[5-(3-Chloro-phenyl)-[1,2,4]oxadiazol-3-yl]-ethoxy}-4-methyl-4H-[1,2,4]triazol-3-yl)-1H-pyridin-2-one Procedure 1

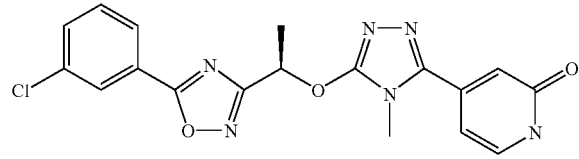

TBAF (1.0 M in THF, 37.4 mL, 37.4 mmol) was added to a mixture of example 35.4 (6.59 g, 12.4 mmol) in THF (116 mL) and the reaction mixture was heated at 55° C. for 3 hours. A small amount of starting material continued to remain therefore additional TBAF (6.2 mL, 6.2 mmol) was added. The reaction mixture was heated further at 55° C. for 30 minutes. The reaction mixture was cooled to room temperature and concentrated. The residue was diluted with dichloromethane, washed three times with water, dried over sodium sulfate and concentrated. The residue was purified by silica gel using dichloromethane:2 M NH₃ in MeOH (100:0 to 94:6) to give the product. The isolated product was triturated with a mixture of diethyl ether and methanol to give the final product (2.43 g, 49%).

¹H NMR (300 MHz, CDCl₃) δ 8.15 (t, 1H), 8.02 (m, 1H), 7.58 (m, 1H), 7.48 (m, 2H), 6.88 (dd, 1H), 6.8 (d, 1H), 6.41 (q, 1H), 3.67 (s, 3H), 1.96 (d, 3H).

Procedure 2

The title compound from example 35.4 (8.8 g, 16.6 mmol) was dissolved in dichloromethane (130 mL) and stirred under nitrogen at 0° C. Dimethyl aluminum chloride (1 M solution in hexanes, 66.5 mL, 66.5 mmol) was added slowly via a syringe to the reaction mixture. The reaction was then warmed to room temperature and stirred until TLC analysis showed that the starting material was consumed (~2 h). The reaction was then cooled again to 0° C. and quenched by careful addition of methanol (5 mL), drop-wise. The reaction was then stirred with a solution of citric acid (40 g) in water (200 mL) for 1 h. The organic phase was separated and the aqueous phase was extracted twice more with chloroform. The combined organics were then washed once with water, dried over magnesium sulfate, filtered and concentrated. The residue was chromatographed on silica gel in 0-10% methanol in a 1:1 mixture of ethyl acetate and dichloromethane to yield the desired product which was triturated from diethyl ether and isolated by filtration.

Chiral Purity (>99%) determined using Chiralpak AD with EtOH:Isopropanol (50:50) with flow rate of 1 mL/min and temperature at 40° C. Retention time is 6.49 minutes.

The following compounds were prepared in a similar fashion:

| Example | Structure | Name | Yield |
|---|---|---|---|
| 38.2 | 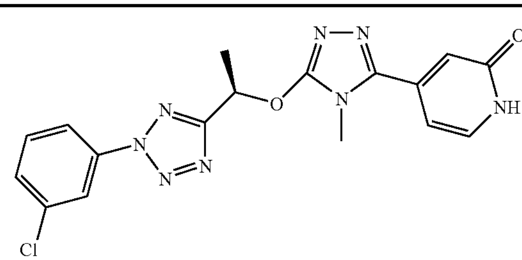 | 4-(5-{(1R)-1-[2-(3-chlorophenyl)-2H-tetrazol-5-yl]ethoxy}-4-methyl-4H-1,2,4-triazol-3-yl)pyridin-2(1H)-one | 103.9 mg<br>55%<br>White solid |

¹H NMR (300 MHz, CDCl₃) δ 1.99 (d, 3 H); 3.62 (s, 3 H); 6.56 (q, 1 H); 6.77 (s, 1 H); 6.81 (d, 1 H); 7.47 (m, 3 H); 8.00 (m, 1 H); 8.11 (s, 1 H)

Example 38.3

5-(5-{1-[2-(3-Chloro-phenyl)-2H-tetrazol-5-yl]-ethoxy}-4-methyl-4H-[1,2,4]triazol-3-yl)-2H-pyridazin-3-one

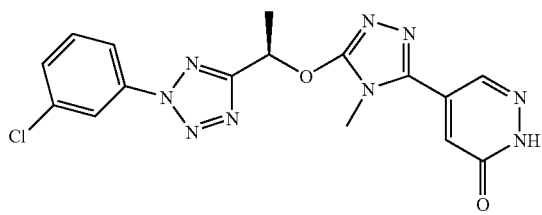

The title compound from Example 35.3 (0.136 g, 0.26 mmol) was dissolved in dichloromethane (2.5 mL) and cooled to 0° C. Dimethyl aluminum chloride (11.0M in hexanes, 1.5 mL) was added and the reaction was stirred at 0° C. for 30 min. and warmed to r.t. for 1 hour. The reaction was quenched with methanol (0.5 mL) citric acid (0.5 g) in water (3 mL). The reaction mixture was extracted with portions of chloroform and the organic extracts were dried over sodium sulfate, filtered and concentrated. The product was purified by column chromatography (1% 2M $NH_3$ in MeOH/dichloromethane) to give the title compound (0.025 g, 24%).

$^1$H NMR (300 MHz, CDCl$_3$) δ 10.90 (s, 1H), 8.48 (d, 1H), 8.17 (s, 1H), 8.06 (m, 1H), 7.51 (m, 2H), 7.09 (d, 1H), 6.61 (q, 1H), 3.70 (s, 3H), 2.04 (d, 3H).

In a similar manner the following compounds were synthesized:

| Example | Structure | Name | Yield |
|---|---|---|---|
| 38.4 | 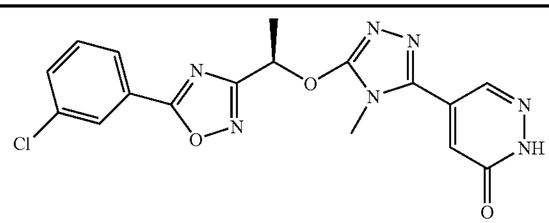 | 5-(5-{1-[5-(3-Chloro-phenyl)-[1,2,4]oxadiazol-3-yl]-ethoxy}-4-methyl-4H-[1,2,4]triazol-3-yl)-2H-pyridazin-3-one | 37% 0.015 g |
| $^1$H NMR | (300 MHz, CDCl$_3$) δ 11.18 (s, 1 H), 8.49 (d, 1 H), 8.14 (s, 1 H), 8.03 (d, 1 H), 7.60 (m, 1 H), 7.50(t, 1 H), 7.11 (d, 1 H), 6.42 (q, 1 H), 3.71 (s, 3 H), 1.97 (d, 3 H) | | |
| 38.5 | 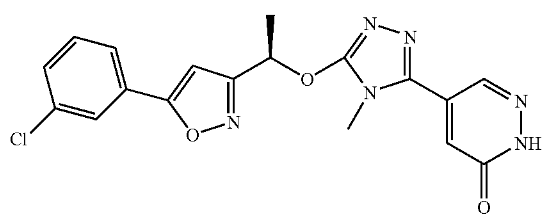 | 5-(5-{1-[5-(3-Chloro-phenyl)-isoxazol-3-yl]-ethoxy}-4-methyl-4H-[1,2,4]triazol-3-yl)-2H-pyridazin-3-one | 39% 0.042 g |
| $^1$H NMR | (300 MHz, CDCl$_3$) δ 11.10 (s, 1 H), 8.49 (d, 1 H), 7.77 (s, 1 H), 7.67 (m, 1 H), 7.44 (m, 2 H), 7.10 (d, 1 H), 6.70 (s, 1 H), 6.37 (q, 1 H), 3.68 (s, 3 H), 1.94 (d, 3 H) | | |
| 38.6 | 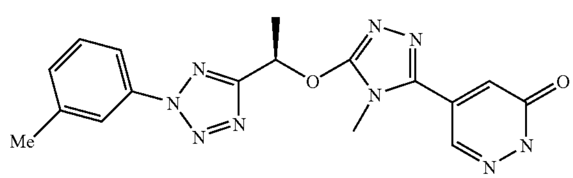 | 5-{4-Methyl-5-[(R)-1-(2-m-tolyl-2H-tetrazol-5-yl)-ethoxy]-4H-[1,2,4]triazol-3-yl}-2H-pyridazin-3-one | 20% 0.089 g |
| $^1$H NMR | (300 MHz, CDCl$_3$) δ 10.79 (s, 1 H), 8.49 (d, 1 H), 7.94 (m, 2 H), 7.45 (t, 1 H), 7.33 (m, 1 H), 7.09 (d, 1 H), 6.62 (q, 1 H), 3.69 (s, 3 H), 2.49 (s, 3 H), 2.05 (d, 3 H) | | |
| 38.7 | 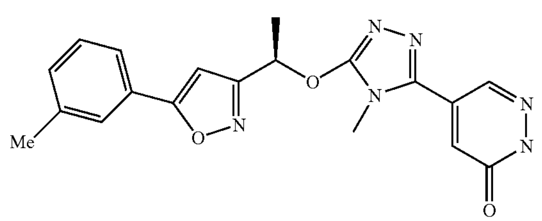 | 5-{4-Methyl-5-[(R)-1-(5-m-tolyl-isoxazol-3-yl)-ethoxy]-4H-[1,2,4]triazol-3-yl}-2H-pyridazin-3-one | 55% 0.050 g |
| $^1$H NMR | (300 MHz, CDCl$_3$) δ 11.18 (s, 1 H), 8.50 (d, 1 H), 7.58 (m, 2 H), 7.34 (t, 1 H), 7.27 (m, 1 H), 7.10 (d, 1 H), 6.66 (s, 1 H), 6.38 (q, 1 H), 3.67 (s, 3 H), 2.42 (s, 3 H), 1.94 (d, 3 H) | | |

Biological Evaluation

Functional Assessment of mGluR5 Antagonism in Cell Lines Expressing mGluR5D

The properties of the compounds of the invention can be analyzed using standard assays for pharmacological activity. Examples of glutamate receptor assays are well known in the art as described in for example Aramori et al., *Neuron* 8:757 (1992), Tanabe et al., *Neuron* 8:169 (1992), Miller et al., *J. Neuroscience* 15: 6103 (1995), Balazs, et al., *J. Neurochemistry* 69:151 (1997). The methodology described in these publications is incorporated herein by reference. Conveniently, the compounds of the invention can be studied by means of an assay (FLIPR) that measures the mobilization of intracellular calcium, $[Ca^{2+}]_i$ in cells expressing mGluR5 or another assay (IP3) that measures inositol phosphate turnover.

FLIPR Assay

Cells expressing human mGluR5d as described in WO97/05252 are seeded at a density of 100,000 cells per well on collagen coated clear bottom 96-well plates with black sides and experiments are done 24 h following seeding. All assays are done in a buffer containing 127 mM NaCl, 5 mM KCl, 2 mM MgCl$_2$, 0.7 mM NaH$_2$PO$_4$, 2 mM CaCl$_2$, 0.422 mg/mL NaHCO$_3$, 2.4 mg/mL HEPES, 1.8 mg/mL glucose and 1 mg/mL BSA Fraction IV (pH 7.4). Cell cultures in the 96-well plates are loaded for 60 minutes in the above mentioned buffer containing 4 µM of the acetoxymethyl ester form of the fluorescent calcium indicator fluo-3 (Molecular Probes, Eugene, Oreg.) in 0.01% pluronic acid (a proprietary, non-ionic surfactant polyol—CAS Number 9003-11-6). Following the loading period the fluo-3 buffer is removed and replaced with fresh assay buffer. FLIPR experiments are done using a laser setting of 0.800 W and a 0.4 second CCD camera shutter speed with excitation and emission wavelengths of 488 nm and 562 nm, respectively. Each experiment is initiated with 160 µl of buffer present in each well of the cell plate. A 40 µl addition from the antagonist plate was followed by a 50 µL addition from the agonist plate. A 30 minute interval separates the antagonist and agonist additions. The fluorescence signal is sampled 50 times at 1 second intervals followed by 3 samples at 5 second intervals immediately after each of the two additions. Responses are measured as the difference between the peak height of the response to agonist, less the background fluorescence within the sample period. IC$_{50}$ determinations are made using a linear least squares fitting program.

IP3 Assay

An additional functional assay for mGluR5d is described in WO97/05252 and is based on phosphatidylinositol turnover. Receptor activation stimulates phospholipase C activity and leads to increased formation of inositol 1,4,5,triphosphate (IP$_3$). GHEK stably expressing the human mGluR5d are seeded onto 24 well poly-L-lysine coated plates at 40×10$^4$ cells/well in media containing 1 µCi/well [3H] myo-inositol. Cells were incubated overnight (16 h), then washed three times and incubated for 1 h at 37° C. in HEPES buffered saline (146 mM NaCl, 4.2 mM KCl, 0.5 mM MgCl$_2$, 0.1% glucose, 20 mM HEPES, pH 7.4) supplemented with 1 unit/mL glutamate pyruvate transaminase and 2 mM pyruvate. Cells are washed once in HEPES buffered saline and preincubated for 10 min in HEPES buffered saline containing 10 mM LiCl. Compounds are incubated in duplicate at 37° C. for 15 min, then either glutamate (80 µM) or DHPG (30 µM) is added and incubated for an additional 30 min. The reaction is terminated by the addition of 0.5 mL perchloric acid (5%) on ice, with incubation at 4° C. for at least 30 min. Samples are collected in 15 mL is polypropylene tubes and inositol phosphates are separated using ion-exchange resin (Dowex AG1-X8 formate form, 200-400 mesh, BIORAD) columns. Inositol phosphate separation was done by first eluting glycero phosphatidyl inositol with 8 mL 30 mM ammonium formate. Next, total inositol phosphates is eluted with 8 mL 700 mM ammonium formate/100 mM formic acid and collected in scintillation vials. This eluate is then mixed with 8 mL of scintillant and [3H] inositol incorporation is determined by scintillation counting. The dpm counts from the duplicate samples are plotted and IC$_{50}$ determinations are generated using a linear least squares fitting program.

Abbreviations

BSA Bovine Serum Albumin

CCD Charge Coupled Device

CRC Concentration Response Curve

DHPG 3,5-dihydroxyphenylglycine

DPM Disintegrations per Minute

EDTA Ethylene Diamine Tetraacetic Acid

FLIPR Fluorometric Imaging Plate reader

GHEK GLAST-containing Human Embryonic Kidney

GLAST glutamate/aspartate transporter

HEPES 4-(2-hydroxyethyl)-1-piperazineethanesulfonic acid (buffer)

IP$_3$ inositol triphosphate

Generally, the compounds were active in the assay above with IC$_{50}$ values less than 10 000 nM. In one aspect of the invention, the IC$_{50}$ value is less than 1 000 nM. In a further aspect of the invention, the IC$_{50}$ value is less than 100 nM. below are data for selected examples, in the FLIPR assay.

| Example No. | FLIPR mGluR5 IC$_{50}$ (nM) |
| --- | --- |
| 36.1 | 19 |
| 36.2 | 20 |
| 37.2 | >3000, >3000, 1576 |
| 37.3 | 10 |
| 38.1 | 13 |
| 38.2 | 9 |
| 38.3 | 6 |
| 38.4 | 15 |
| 38.5 | 8 |
| 38.6 | 7 |
| 38.7 | 12 |

Determination of Brain to Plasma Ratio ("B/P Ratio") in Rat

Brain to plasma ratios are estimated in female Sprague Dawley rats. The compound is dissolved in water or another appropriate vehicle. For determination of brain to plasma ratio the compound is administrated as a subcutaneous, or an intravenous bolus injection, or an intravenous infusion, or an oral administration. At a predetermined time point after the administration a blood sample is taken with cardiac puncture. The rat is terminated by cutting the heart open, and the brain is immediately retained. The blood samples are collected in heparinized tubes and centrifuged within 30 minutes, in order to separate the plasma from the blood cells. The plasma is transferred to 96-well plates and stored at −20° C. until analysis. The brains are divided in half, and each half is placed in a pre-tarred tube and stored at −20° C. until analysis. Prior to the analysis, the brain samples are thawed and 3 mL/g brain tissue of distilled water is added to the tubes. The brain samples are sonicated in an ice bath until the samples are homogenized. Both brain and plasma samples are precipitated with acetonitrile. After centrifugation, the supernatant is diluted with 0.2% formic acid. Analysis is performed on a short reversed-phase HPLC column with rapid gradient elution and MSMS detection using a triple quadrupole instrument with electrospray ionisation and Selected Reaction Monitoring (SRM) acquisition. Liquid-liquid extraction may be used as an alternative sample clean-up. The samples are extracted, by shaking, to an organic solvent after addition of a suitable buffer. An aliquot of the organic layer is transferred to a new vial and evaporated to dryness under a stream of nitrogen. After reconstitution of the residuals the samples are ready for injection onto the HPLC column.

Generally, the compounds according to the present invention are peripherally restricted with a drug in brain over drug in plasma ratio in the rat of <0.5. Shown in the table below is a ratio for a representative compound of the invention. For comparison purposes, the corresponding ratio for a compound known in the art is also presented.

swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 mL/kg) in a foreleg vein. Ten min after i.v. administration, a nutrient meal (10% peptone, 5% D-glucose, 5% Intralipid, pH 3.0) is infused into the stomach through the central lumen of the assembly at 100 mL/min to a final volume of 30 mL/kg. The infusion of the nutrient meal is followed by air infusion at a rate of 500 mL/min until an intragastric pressure of 10±1 mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal≦2 s before its onset in which case the relaxation is classified as swallow-induced. The pressure difference between the LES and the stomach should be less than 2 mmHg, and the duration of the complete relaxation longer than 1 s.

| Example | Structure | B/P Ratio | Comparison Compound | B/P Ratio |
|---|---|---|---|---|
| 37.3 | 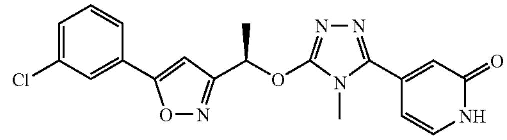 | 0.02 | | 0.80 |

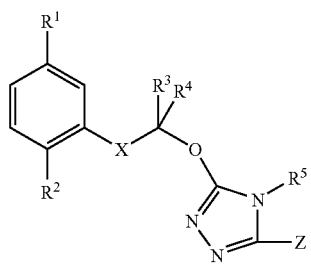

Screening for Compounds Active Against TLESR

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure

The invention claimed is:
1. A compound of formula (I)

(I)

wherein
$R^1$ is selected from methyl and chloro;
$R^2$ is hydrogen;
$R^3$ is methyl;
$R^4$ is hydrogen;
$R^5$ is methyl;

X is selected from the group consisting of:

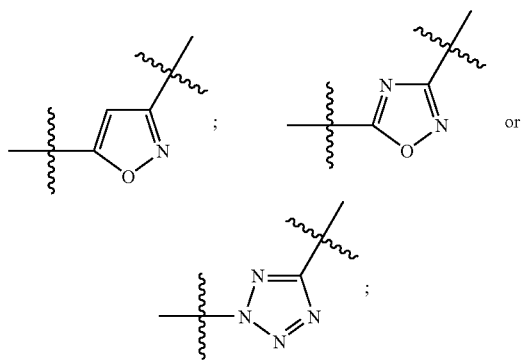

and Z is selected from the group consisting of:

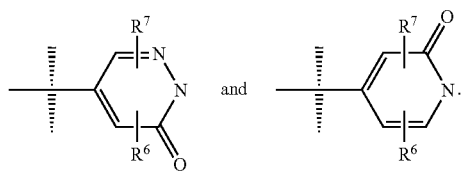

wherein
R$^6$ is hydrogen;
R$^7$ is hydrogen;

or a pharmaceutically acceptable salt, hydrate, tautomer or enantiomer thereof.

2. A compound selected from the group consisting of:
5-(5-{(1R)-1-[2-(3-Chlorophenyl)-2H-tetrazol-5-yl]ethoxy}-4-methyl-4H-1,2,4-triazol-3-yl)pyridazin-3(2H)-one;

5-(4-Methyl-5-{(1R)-1-[2-(3-methylphenyl)-2H-tetrazol-5-yl]ethoxy}-4H-1,2,4-triazol-3-yl)pyridazin-3(2H)-one; and 5-(5-{(1R)-1-[5-(3-Chlorophenyl)isoxazol-3-yl]ethoxy}-4-methyl-4H-1,2,4-triazol-3-yl)pyridazin-3(2H)-one.

3. The compound 5-(5-{(1R)-1-[2-(3-Chlorophenyl)-2H-tetrazol-5-yl]ethoxy}-4-methyl-4H-1,2,4-triazol-3-yl)pyridazin-3(2H)-one or a pharmaceutically acceptable salt, hydrate, tautomer or enantiomer thereof.

4. The compound 5-(4-Methyl-5-{(1R)-1-[2-(3-methylphenyl)-2H-tetrazol-5-yl]ethoxy}-4H-1,2,4-triazol-3-yl)pyridazin-3(2H)-one or a pharmaceutically acceptable salt, hydrate, tautomer or enantiomer thereof.

5. The compound 5-(5-{(1R)-1-[5-(3-Chlorophenyl)isoxazol-3-yl]ethoxy}-4-methyl-4H-1,2,4-triazol-3-yl)pyridazin-3(2H)-one or a pharmaceutically acceptable salt, hydrate, tautomer or enantiomer thereof.

6. A pharmaceutical composition comprising a compound according to any one of claims 1-5 as an active ingredient, together with a pharmacologically and pharmaceutically acceptable carrier.

* * * * *